(12) United States Patent
Hofmann et al.

(10) Patent No.: US 9,907,523 B2
(45) Date of Patent: Mar. 6, 2018

(54) X-RAY DETECTOR AND X-RAY SYSTEM

(71) Applicant: Fraunhofer-Gesellschaft zur Foerderung der angewandten Forschung e.V., Munich (DE)

(72) Inventors: Thomas Hofmann, Grossenseebach (DE); Stefan Hebele, Nuremberg (DE); Thomas Schlechter, Hoechstadt (DE)

(73) Assignee: FRAUNHOFER-GESELLSCHAFT ZUR FOERDERUNG DER ANGEWANDTEN FORSCHUNG E.V., Munich (DE)

( * ) Notice: Subject to any disclaimer, the term of this patent is extended or adjusted under 35 U.S.C. 154(b) by 745 days.

(21) Appl. No.: 14/541,264

(22) Filed: Nov. 14, 2014

(65) Prior Publication Data

US 2015/0078525 A1    Mar. 19, 2015

Related U.S. Application Data

(63) Continuation of application No. PCT/EP2013/060122, filed on May 16, 2013.

(30) Foreign Application Priority Data

May 16, 2012   (DE) ........................ 10 2012 208 305

(51) Int. Cl.
*A61B 6/06*       (2006.01)
*H01L 27/146*   (2006.01)
(Continued)

(52) U.S. Cl.
CPC ............ *A61B 6/447* (2013.01); *A61B 6/4233* (2013.01); *A61B 6/4291* (2013.01);
(Continued)

(58) Field of Classification Search
CPC .... A61B 6/00; A61B 6/06; A61B 6/42; A61B 6/4208; A61B 6/4233; A61B 6/4266;
(Continued)

(56) References Cited

U.S. PATENT DOCUMENTS 4,204,123 A      5/1980  Stoddart
4,592,080 A  *  5/1986  Rauch .................... A61B 6/032
                                                                    378/10

(Continued)

FOREIGN PATENT DOCUMENTS

DE              43 05 475 C1      9/1994
DE    10 2006 015 028 A1    10/2007
(Continued)

OTHER PUBLICATIONS

Official Communication issued in International Patent Application No. PCT/EP2013/060122, dated Jan. 23, 2014.
(Continued)

*Primary Examiner* — Anastasia Midkiff
(74) *Attorney, Agent, or Firm* — Keating & Bennett, LLP

(57) ABSTRACT

An X-ray detector has a first detector module, a second detector module and manipulation means. The first detector module includes a first detection region arranged in a first detection plane, the second detector module includes a second detection region arranged in a second detection plane, which is adjacent to the first detection region. The manipulation means is configured to orient the first detection plane of the first detector module and the second detection plane of the second detector module to each other such that a first normal to surface of the first detection plane and a second normal to surface of the second detection plane intersect within a reference region.

30 Claims, 16 Drawing Sheets

(51) Int. Cl.
*H01L 27/148* (2006.01)
*A61B 6/00* (2006.01)
*G01T 1/24* (2006.01)

(52) U.S. Cl.
CPC .. *H01L 27/14601* (2013.01); *H01L 27/14636* (2013.01); *H01L 27/14806* (2013.01); *A61B 6/4266* (2013.01); *A61B 6/4452* (2013.01); *A61B 6/587* (2013.01); *A61B 2562/164* (2013.01); *G01T 1/243* (2013.01)

(58) Field of Classification Search
CPC ....... A61B 6/4275; A61B 6/4291; A61B 6/44; A61B 6/4411; A61B 6/4429; A61B 6/447; A61B 6/587; A61B 6/588; A61B 2562/00; A61B 2562/02; A61B 2562/04; A61B 2562/043; A61B 2562/046; A61B 2562/16; A61B 2562/164; A61B 2562/166; H01L 27/14; H01L 27/144; H01L 27/146; H01L 27/1446; H01L 27/14601; H01L 27/14618; H01L 27/14634; H01L 27/14636; H01L 27/14658; H01L 27/14676; H01L 27/14683; H01L 27/1469; H01L 27/148; H01L 27/14806; H01L 27/14825; H01L 27/14831; H01L 21/48; H01L 21/485; H01L 21/4871; H01L 21/71; H01L 24/72; H01L 24/74; H01L 24/741; H01L 24/90; H01L 24/91; G21K 1/00; G21K 1/10; G21K 2201/00; G21K 2201/067; G21K 2224/63; G21K 2224/71; G21K 2224/72; G21K 2224/73; G21K 2224/75753; G21K 2224/75754; G21K 2224/758; G21K 2224/75801–2224/75803; G21K 2224/75821–2224/75823; G21K 2224/80; G21K 2224/80001; G21K 2224/80007; G21K 2224/80051; G21K 2224/8009; G21K 2224/8012; G21K 2224/80136; G21K 2224/80138; G21K 2224/80139; G21K 2224/8014; G21K 2224/80141; G21K 2224/80148; G21K 2224/80149; G21K 2224/8015; G21K 2224/80169; G21K 2224/8017; G21K 2224/8038; G21K 2224/80897; G21K 2224/80898; G21K 2224/80899; G21K 2224/84; G21K 2224/85; G21K 2224/89;
See application file for complete search history.

(56) References Cited

U.S. PATENT DOCUMENTS

| | | | |
|---|---|---|---|
| 5,349,190 A | 9/1994 | Hines et al. | |
| 6,242,743 B1 | 6/2001 | DeVito et al. | |
| 6,583,418 B1 | 6/2003 | Deckers et al. | |
| 6,583,420 B1 | 6/2003 | Nelson et al. | |
| 7,560,702 B2 * | 7/2009 | Meirav | A61B 6/032 250/370.09 |
| 7,592,597 B2 | 9/2009 | Hefetz et al. | |
| 7,723,689 B2 | 5/2010 | Vija | |
| 7,838,838 B2 | 11/2010 | Rousso et al. | |
| 8,098,795 B2 | 1/2012 | Nowak et al. | |
| 8,173,969 B2 | 5/2012 | Nishino et al. | |
| 9,066,649 B2 * | 6/2015 | Roessl | A61B 6/00 |
| 2004/0021083 A1 * | 2/2004 | Nelson | A61B 6/4233 250/370.09 |
| 2005/0094763 A1 * | 5/2005 | Sherman | A61B 6/032 378/19 |
| 2007/0183562 A1 * | 8/2007 | Popescu | A61B 6/032 378/19 |
| 2008/0039721 A1 | 2/2008 | Shai et al. | |
| 2008/0272309 A1 | 11/2008 | Schweizer et al. | |
| 2012/0183119 A1 * | 7/2012 | Ikhlef | A61B 6/035 378/19 |
| 2014/0314196 A1 * | 10/2014 | Zou | A61B 6/032 378/4 |

FOREIGN PATENT DOCUMENTS

| | | |
|---|---|---|
| DE | 10 2007 035 673 A1 | 2/2008 |
| DE | 10 2009 045 092 A1 | 12/2010 |
| EP | 2 105 762 A1 | 9/2009 |
| JP | 2002-535629 A | 10/2002 |
| JP | 2008-504520 A | 2/2008 |
| WO | 02/079802 A2 | 10/2002 |
| WO | 2008/135994 A2 | 11/2008 |
| WO | 2009/125309 A2 | 10/2009 |
| WO | 2011/149181 A2 | 12/2011 |

OTHER PUBLICATIONS

Official Communication issued in corresponding Japanese Patent Application No. 2015-512056, dated Jun. 6, 2017.

* cited by examiner

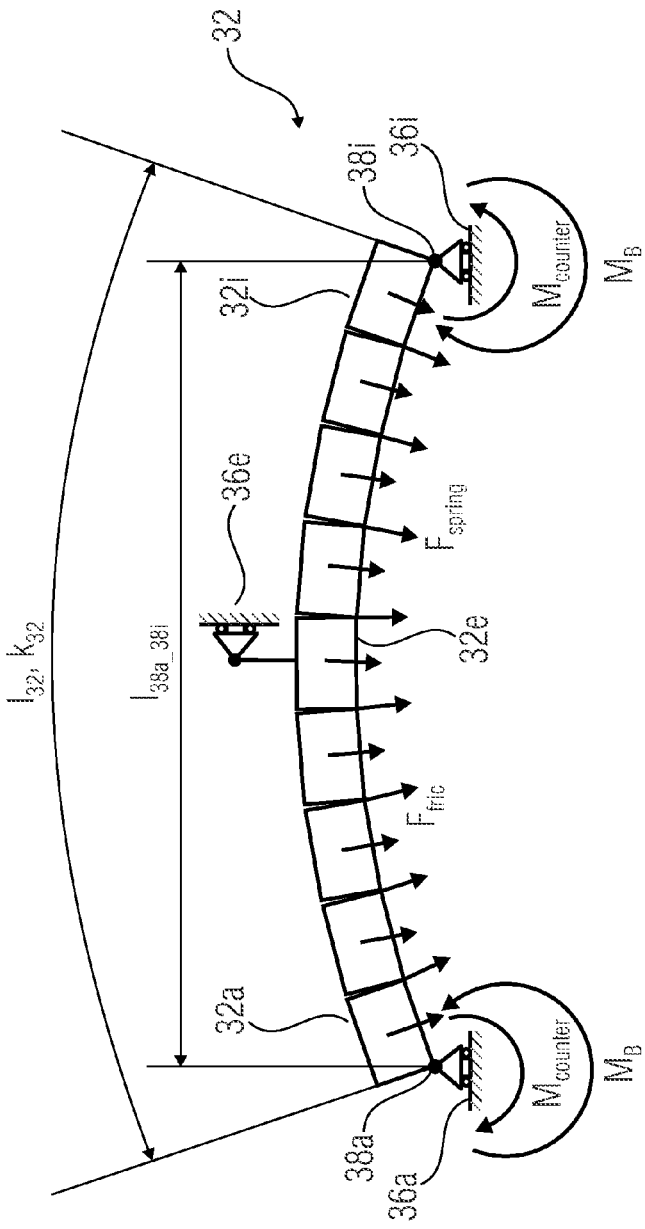
FIGURE 3A
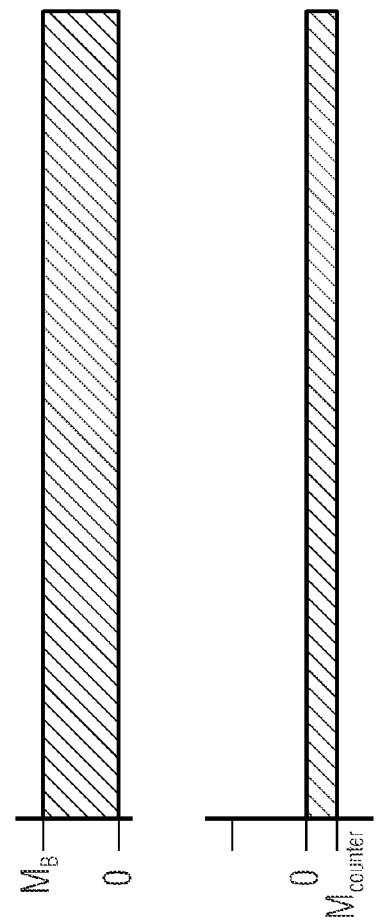
FIGURE 3B
FIGURE 3C

X-RAY DETECTOR AND X-RAY SYSTEM

CROSS-REFERENCE TO RELATED APPLICATIONS

This application is a continuation of International Application No. PCT/EP2013/060122, filed May 16, 2013, which is incorporated herein by reference in its entirety, and additionally claims priority from German Application No. 102012208305.7, filed May 16, 2012, which is also incorporated herein by reference in its entirety.

BACKGROUND OF THE INVENTION

Embodiments of the present invention relate to an X-ray system, an X-ray detector and, in particular, to an X-ray detector comprising an adjustable radius of curvature.

X-ray detectors, such as, for example, CCD sensors comprising scintillators, are included in X-ray systems in order to detect an absorption profile which results from transmission of an object by X-radiation and allows drawing conclusions as to a density distribution of the object.

FIG. 7 shows such an X-ray system comprising a radiation source 10 and a detector 12 which is arranged spaced apart from the radiation source 10 at a focus-detector distance $a_{10\_12}$. The detector 12 comprises seven detector modules 12a to 12g, such as, for example, seven detector lines. The radiation source 10, such as, for example, an X-ray tube, represents a point-shaped radiation source of an opening angle $\alpha_{14}$, the X-radiation emitted consequently propagating conically (see light path 14). Since the detector 12 used here is flat, an angle of incidence of the X-radiation (see light path 14) on the detector 12 is dependent on the place of the detector (cf. detector modules 12a to 12g). Thus, a central ray from the radiation source 10 impinges on the detector center or central detector module 12d perpendicularly, whereas the X-radiation impinges on the detector 12 the flatter, the more distant the specific detector module, such as, for example, 12a or 12g, is from the center.

Compared to bent detectors, flat detectors, such as, for example, flat-panel detectors or in particular line detectors 12, excel by their relatively low price and easy manageability, exemplarily with regard to variability of the focus-detector distance $a_{10\_12}$, wherein the image quality, however, may decrease towards the edge regions. This is due to the fact that the portion of the X-radiation 14 crossing a neighboring pixel increases with an angle of incidence becoming flatter (exemplarily in the detector module 12a or 12g). Due to the oblique transmission through the sensor layer, the spatial resolution is deteriorated or, more precisely, a signal is blurred over neighboring pixels. Consequently, this effect is maximal at the edge (cf. detector module 12a or 12g). Another effect is caused by the setup shown of a point-shaped radiation source 10 and a two-dimensional detector 12, namely the fact that different dose rates result from the different distances between the radiation source 10 and the detector modules 12a to 12g. Due to the greater distance, the dose rate on the detector modules 12a and 12g in the edge region is smaller compared to the dose rate on the detector module 12d in the center, resulting in a lower signal and, thus, higher noise (lower signal-to-noise ratio).

Additionally, it is to be mentioned that, with bent detectors (in contrast to flat detectors), as are exemplarily used in gantry systems, the angle of incidence is location-independent or even perpendicular when the focus-detector distance $a_{10\_12}$ (i.e. the distance of the tube-detector system rotating around the object to be measured) is not changed. In particular in industrial applications in which the measuring conditions (such as the positioning of the radiation source 10 relative to the detector 12) change frequently, bent detectors, however, are hardly used due to the invariable focus-detector distance $a_{10\_12}$.

SUMMARY

According to an embodiment, an X-ray detector may have: a first detector module having a first detection region arranged in a first detection plane; a second detector module having a second detection region arranged in a second detection plane, which is neighboring to the first detector module; and manipulation means configured to orient the first detection plane of the first detector module and the second detection plane of the second detector module to each other such that a first normal to surface of the first detection plane and a second surface to normal of the second detection plane intersect within a reference region.

According to another embodiment, an X-ray detector may have: a first detector module having a first detection region arranged in a first detection plane; a second detector module having a second detection region arranged in a second detection plane; a further detector module having a further detection region arranged in a further detection plane; and manipulation means configured to orient the first detection plane of the first detector module, the second detection plane of the second detector module and the further detection plane of the further detector module to one another such that a first normal to surface of the first detection plane, a second surface to normal of the second detection plane and a further normal to surface of the further detection region intersect within a reference region, wherein the first and/or second detection plane(s) is/are offset relative to the further detection plane and the first and/or second detection region(s) is/are overlapped by the further detection region.

According to still another embodiment, an X-ray system may have: an X-ray detector as mentioned above; and a radiation source, wherein the reference region may be positioned by means of the manipulation means in dependence on a focus-detector distance.

According to another embodiment, an X-ray system may have: an X-ray detector as mentioned above; and a radiation source, wherein the radius of the circular path may be adjusted by means of the manipulation means such that a focal spot of the radiation source corresponds to the center of the adjustable radius.

According to another embodiment, an X-ray detector may have: a first detector module having a first detection region arranged in a first detection plane; a second detector module having a second detection region arranged in a second detection plane, which is neighboring to the first detector module; and manipulation means configured to orient the first detection plane of the first detector module and the second detection plane of the second detector module to each other such that a first normal to surface of the first detection plane and a second surface to normal of the second detection plane intersect within a reference region, wherein the X-ray detector has at least a further detector module having a further detection region arranged in a further detection plane, which is arranged relative to the first and second detector modules such that the first, second and further detection planes are distributed with their respective centroids tangentially on a circular path at an adjustable radius; wherein the manipulation means is configured to orient the further detection plane of the further detector module relative to the first and second detection planes such that the first and second normals to surface, together with a further normal to surface of the further detection plane, intersect within the reference region, wherein the manipulation means is configured to provide the first and/or further detector module(s) with a torque, and wherein the first, second and further detector modules are supported relative to one another by means of springs configured to distribute the torque evenly among all the detector modules in order to orient the detector modules along the circular path.

According to another embodiment, an X-ray detector may have: a first detector module having a first detection region arranged in a first detection plane; a second detector module having a second detection region arranged in a second detection plane, which is neighboring to the first detector module; and manipulation means configured to orient the first detection plane of the first detector module and the second detection plane of the second detector module to each other such that a first normal to surface of the first detection plane and a second surface to normal of the second detection plane intersect within a reference region, wherein the X-ray detector has at least a further detector module having a further detection region arranged in a further detection plane, which is arranged relative to the first and second detector modules such that the first, second and further detection planes are distributed with their respective centroids tangentially on a circular path at an adjustable radius; wherein the manipulation means is configured to orient the further detection plane of the further detector module relative to the first and second detection planes such that the first and second normals to surface, together with a further normal to surface of the further detection plane, intersect within the reference region, wherein the first and second detector modules are connected relative to each other by a first spring and the second and further detector modules are connected relative to each other by a second spring, the first and second springs having equal spring stiffness, wherein the manipulation means is configured to vary a distance between the first and further detector modules, and wherein the first, second and further detector modules are connected by means of springs configured to orient the X-ray detector along the circular path when varying the distance.

Embodiments of the present invention provide an X-ray detector comprising a first detector module, a second detector module and manipulation means. The detector modules may exemplarily comprise one or several sensor elements in one or several planes (two-dimensional area detector), and include respective electronics and mechanics. The first detector module includes a first detection region arranged in a first detection plane, the second detector module includes a second detection region arranged in a second detection plane, which is neighboring or adjacent to the first detection region. The manipulation means is configured to orient the first detection plane of the first detector module and the second detection plane of the second detector module to each other such that a first normal to surface of the first detection plane and a second normal to surface of the second detection plane intersect within a reference region.

Embodiments of the present invention are based on detector modules to be arranged on an arc of a circle at a flexibly adjustable radius of curvature. Due to the circular arc arrangement of the detector modules, all the normals to surface thereof can meet in a reference region, exemplarily at the location of the radiation sources, which is equivalent to focusing the detector modules onto the radiation source. Thus, the X-radiation will impinge on the individual detector modules perpendicularly and an influence (blurring) of neighboring pixels as a consequence of oblique transmission can be minimized. The radius of curvature adjustable by means of manipulation means, such as, for example, an actuator, allows the respective detection region or the respective normal to surface to be orientated to the radiation source specifically for each detector module. The adjustability offers the advantage that exact focusing may even be achieved when the focus-detector distance has been changed, exemplarily as a consequence of a varied measuring setup. Additionally, with a bent X-ray detector arrangement, the radiation dose of the X-radiation incident on the individual detector modules is not dependent on which detector module the X-radiation impinges on, since the distance between the radiation source and each detector module will be the same, due to the circular arrangement, when the detector modules are oriented to the radiation source or a focal spot of the radiation source. Thus, apart from the spatial resolution, the noise performance may at the same time be improved to a constant good value over the entire detection region.

According to further embodiments, the individual detector modules are supported flexibly relative to one another, exemplarily using a spring or another flexible mechanic connection, such that they may be arranged along the desired radius of curvature. For arranging or exactly adjusting the radius of curvature, the manipulation means may be configured to orient two or more detector modules evenly along a circular arc.

Another embodiment provides an X-ray detector comprising a first detector module, a second detector module, a further detector module and manipulation means. The first detector module comprises a first detection region arranged in a first detection plane, the second detector module comprises a second detection region arranged in a second detection plane, and the further detector module comprises a further detection region arranged in a further detection plane. The first and/or second detection plane(s) is/are offset relative to the further detection plane, the first and/or second detection region(s) being overlapped by the further detection region. The manipulation means is configured to orient the first detection plane of the first detector module, the second detection plane of the second detector module and the further detection plane of the further detector module such that a first normal to surface of the first detection plane, a second normal to surface of the second detection plane and a further normal to surface of the further detection plane intersect within a reference region. Advantageously, the individual detector modules here are arranged one behind the other in two different rows such that the entire detection plane may be detected by the overlapping first, second and further detection planes, without any so-called "dead regions" forming at the rotation axis between two adjacent detector modules adjustable with regard to their normals to surface.

BRIEF DESCRIPTION OF THE DRAWINGS

Embodiments of the present invention will be detailed referring to the appended drawings, in which:

FIG. 3a-c show schematic basic illustrations of manipulation means in accordance with an embodiment, in connection with diagrams for illustrating the forces and moments occurring;

DETAILED DESCRIPTION OF THE INVENTION

Figure 1:
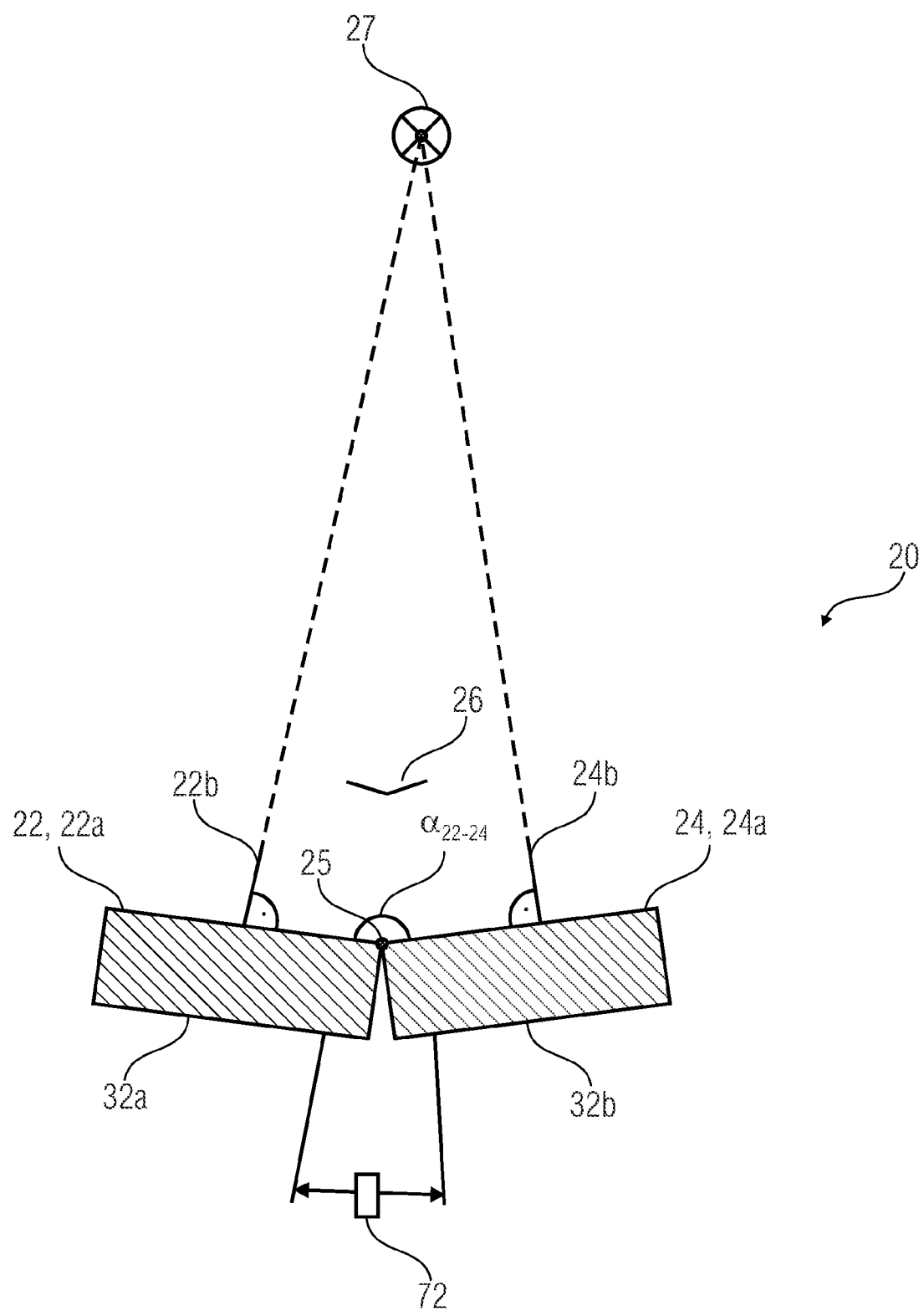
FIG. 1 shows a schematic basic illustration of an X-ray detector having an adjustable radius of curvature in accordance with an embodiment.

Before embodiments will be discussed in greater detail with reference to the Figures, it is pointed out that same elements or elements of equal effect are provided with same reference numerals such that the description thereof is mutually applicable or exchangeable.

FIG. 1 shows an X-ray detector 20 comprising a first detector module 32a and a second detector module 32b with which manipulation means 72 is engaged for exactly positioning same. The first detector module 32a comprises a first detection region 22a arranged in a first detection plane 22, the second detector module 32b comprises a second detection region 24a arranged in a second detection plane 24, the two detection regions 22a and 24a being arranged such that they are neighboring or even directly abutting onto each other and facing incident X-radiation 26 emitted by a radiation source 27. The two detector modules 32a and 32b are at an angle relative to each other (cf. angle $\alpha_{22\_24}$) or arranged on a circular path around the radiation source 27 such that each detector module 32a and 32b is oriented directly to the radiation source 27. In other words, the detection planes 22 and 24 intersect in an axis 25, namely the rotation axis 25 of the two detector modules 32a and 32b such that a first normal to surface 22b of the first detection plane 22 and a second normal to surface 24b of the second detection plane 24 are directed towards the radiation source 27 or intersect within a reference region of the radiation source 27.

The conditions of detection will be the better, the smaller the reference region within which the radiation source 27 (or the focal spot thereof) is positioned. Thus, the conditions of detection are optimum when the two normals to surface 22b and 24b intersect at the place of the radiation source 27 (focal spot). Since the focus-detector distance is not fixed, in particular in industrial systems, the two normals to surface 22b and 24b and the arrangement of the two normals to surface 22b and 24b may be adjusted relative to each other. Focusing the two detector modules 32a and 32b onto the radiation source 27 here may be post-adjusted in correspondence with a focus-detector distance chosen (distance between the detector 20 and the radiation source 27) by means of the manipulation means 72, or the position of the reference region or intersection of the two normals to surface 22b and 24b be varied such that they intersect close to or in the focal spot of the radiation source 27. The angle $\alpha_{22\_24}$ between the two detector modules 32a and 32b here may, for example, be varied in dependence on the focus-detector distance chosen using the manipulation means 72 which, for example, twists the two detector modules 32a and 32b relative to each other. This means that this concept allows ensuring a perpendicular angle of incidence on the X-radiation 26 onto the detector modules 32a and 32b, which results in an improved imaging precision (exemplarily higher signal-to-noise ratio and/or smaller signal blurring). In addition, when using the X-ray detector 20, the flexibility of the X-ray system is increased since both small and large objects (i.e. varying the focus-detector distance) may be examined with different spatial resolutions using the same measuring system.

According to further embodiments, the detector modules 32a and 32b are placed such that they contact or nearly contact the edge (cp. rotational axis 25) of that side facing the X-radiation 26 (cp. detection region 22a or 24a). This serves for allowing no or only very small gaps and thus small "non-detection regions" or "dead regions" to form between the first and second detection regions 22a and 24a. This contacting edge at the same time is the rotational axis 25 (or the center of rotation 25) around which the detector module 32a and 32b move relative to each other when varying the angle $\alpha_{22\_32b}$. This rotational axis 25 may exemplarily be defined by the positioning of the detector modules 32a and 32b. An example of this would be positioning the detector modules 32a and 32b relative to each other by a common spring by means of which they are connected, wherein the rotational axis 25 is defined by a bending point of the spring. The geometry of motion of the detector modules 32a and 32b may be determined precisely by means of additional spacers.

Figure 2A:
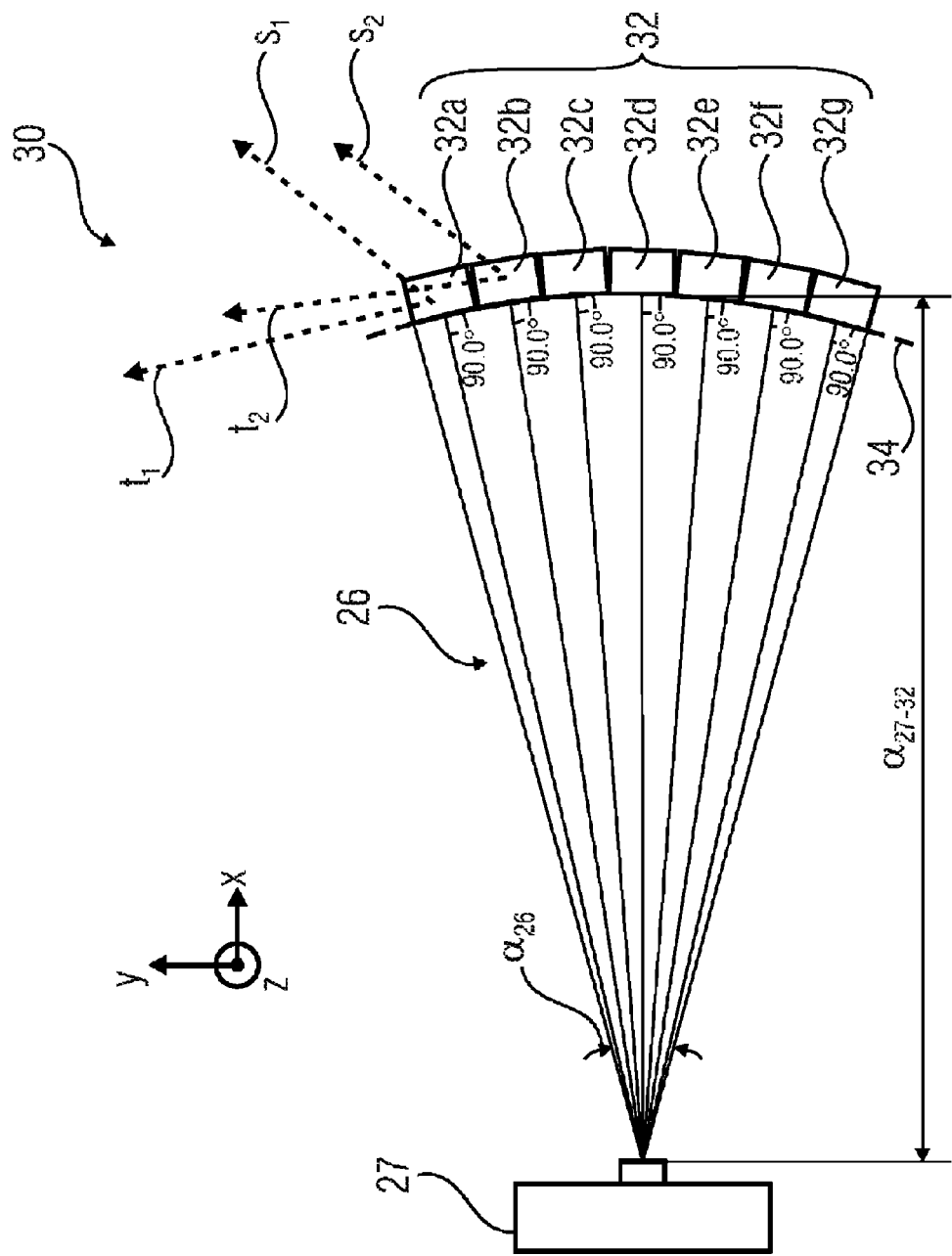
FIGS. 2a-b show schematic basic illustrations of an X-ray system in accordance with an embodiment.
Figure 2B:
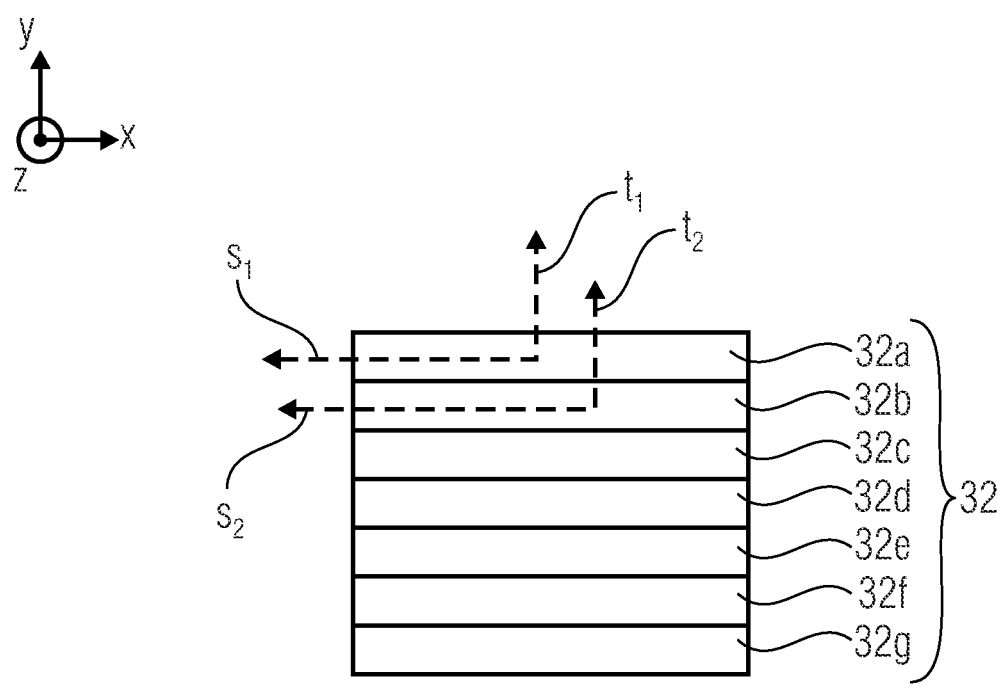

FIG. 2a shows an X-ray system 30 comprising a detector 32 and a radiation source 27 which emits X-radiation 26 conically. The X-ray system 30 in FIG. 2a is illustrated in the X-ray plane as the plane of the drawing, whereas the detector 32 in FIG. 2b is illustrated in the zy-plane (perpendicular to the xy-plane). In this embodiment, the detector 32 comprises a plurality of detector modules 32a to 32g which are arranged circularly along a circular arc 34, wherein the detector modules 32a to 32g basically correspond to the detector modules 32a and 32b of FIG. 1. In other words, this means that a bent line detector is formed by the circular arrangement of the detector modules 32a to 32g, wherein the plurality of detector modules 32a to 32g are arranged tangentially next to one another or directly adjacent to one another on the circular arc 34 such that the detection area shaped like a cylinder surface spanned by an emission angle $\alpha_{26}$ of the X-radiation 26 may be detected over all the detection regions of the detector modules 32a to 32g. Consequently, the result is that all the normals to surface which exemplarily act on the center of gravity of the detector modules 32a to 32g are arranged in a so-called normal plane which intersects the reference region. It is additionally mentioned that the individual detector modules 32a to 32g may be arranged in parallel to the respective tangent of the circular arc 34, wherein the normal to surface of the respective tangent advantageously intersects the respective detection region in the centroid of the respective detector module 32a to 32g.

The detector modules 32a to 32g may exemplarily be multi-line detectors having a plurality of sensors or pixels in a first direction $s_1$ and second direction $s_2$ (each perpendicular to the circular arc 34) and/or a plurality of sensors or pixels in a third direction $t_1$ and fourth direction $t_2$ (each tangential to the circular arc 34). It is to be mentioned that such detectors 32 are very narrow (exemplarily a few pixels)

in their widths (cf. first and second directions $s_1$ and $s_2$) relative to their lengths (cf. third and fourth directions $t_1$ and $t_2$, i.e. from the detector module $32a$ to the detector module $32g$) such that it is typically sufficient for the detector $32$ to be curved along the longitudinal direction (cp. third and fourth directions $t_1$ and $t_2$). As can be seen in FIG. 2b, the first and second directions $s_1$ and $s_2$ and the third and fourth directions $t_1$ and $t_2$ (in the projection illustrated) are each parallel to each other, wherein the first and second directions $s_1$ and $s_2$ are perpendicular relative to the third and fourth directions $t_1$ and $t_2$.

A normal to surface which extends perpendicularly from the surface of the respective detection region is indicated for each of these detector modules $32a$ to $32g$, wherein all the normals to surface of the detector modules $32a$ to $32g$ intersect within the reference region or even meet in a common point of intersection which corresponds to the focal spot of the radiation source 27. This means that each normal to surface of the detector modules $32a$ to $32g$ exhibits a length which corresponds to the radius of the circular arc 34 and thus also to a focus-detector distance $a_{27\_32}$ between the radiation source 27 and the X-ray detector 32. This means that each individual detector module $32a$ to $32g$ is at the same distance to the point-shaped radiation source 27 and arranged to be perpendicular to it such that the X-radiation 26 will impinge on the respective detector module $32a$ to $32g$ perpendicularly or, more precisely, on a center or center of gravity of the respective detector module $32a$ to $32g$. It is also to be mentioned that the individual normals to surface to the detection planes of the detector modules $32a$ to $32g$ may be dropped to be perpendicular on the center of gravity of the respective detection planes of the respective detector module $32a$ to $32g$ when the individual detector modules $32a$ to $32g$ are elongate or flat detector modules. The respective centroid corresponds to the center of the rectangular detection area of the individual detector modules $32a$ to $32g$ or the center of the detection region chosen of the respective detector module $32a$ to $32g$. In particular in industrial usage, such as, for example, in high-energy imaging, the device 32 illustrated offers advantages since the corruption of the spatial resolution by oblique transmission here is particularly high due to the thick sensor layers employed.

In analogy to the embodiment of FIG. 1, the individual normals to surface of the detector modules $32a$ to $32g$ or the radius of the circular arc 34 may be adjusted by means of the manipulation means (not illustrated) such that the X-ray detector 32 may be adapted to different distances $a_{27\_32}$. One way of orienting the normals to surface of the detector modules $32a$ to $32g$ will be discussed below referring to FIGS. 3a to 3c.

FIG. 3a shows the X-ray detector 32 having nine detector modules $32a$ to $32i$ which are connected to one another elastically, for example by means of springs. Thus, two neighboring detector modules each of the detector modules $32a$ to $32i$ are rotatable relative to each other around a common center of rotation or common rotation axis. The rotation axis may exemplarily be formed by contact points or a contact axis of the sensor layer corners, facing the radiation source, of two neighboring detector modules or else be arranged between two detector modules. Furthermore, the entire X-ray detector 32 is supported such that the respective detector modules $32a$ to $32i$ may be adjusted together. Here, the detector module $32a$ is supported by means of a first linear guide $36a$ and the last detector module $32i$ by means of a further linear guide $36i$. At each linear guide $36a$ and $36i$, the X-ray detector 32 is supported rotationally relative to the linear guide $36a$ and $36i$ by means of a rotational support $38a$ and $38i$, respectively. A bending moment $M_b$ may be introduced in the X-ray detector 32 using these rotational supports $38a$ and $38i$, for example, by means of electrical (actuating) motors which represent a manipulation means.

By introducing the bending moment $M_b$ into the detector modules $32a$ to $32i$ connected to one another like an elastic chain, the bending moment $M_b$ is distributed evenly along the nine detector modules $32a$ to $32i$, as is illustrated in FIG. 3b. By means of the even distribution of the bending moment $M_b$ over an entire length $l_{32}$ of the X-ray detector 32, it is bent continuously such that the individual detector modules $32a$ to $32i$ are placed along a circular path or along a circular segment $k_{32}$, wherein the radius of the circular arc (and thus the location of normals to surface) may be adjusted via the bending moment $M_b$. The constant distribution of the bending moment $M_b$ over the length $l_{32}$ is exemplarily achieved by using springs of equal or approximately equal spring stiffness for supporting the individual detector modules $32a$ to $32i$. The consequence of this is that (when introducing a bending moment $M_b$) the same angle forms between each detector module and the next detector module $32a$ to $32i$ or between two normals to surface of neighboring detector modules $32a$ to $32i$. A counter moment $M_{counter}$ which is also distributed evenly over the entire length $M_{32}$ counteracts the bending moment $M_b$, as is illustrated in FIG. 3c. This counter moment $M_{counter}$ results from the spring force $F_{spring}$ and the friction force $F_{fric}$ forming when bending the X-ray detector 32 between the individual detector modules $32a$ to $32i$. It is to be mentioned that the moments $M_b$ and $M_{counter}$ and the forces $F_{spring}$ and $F_{fric}$ are illustrated in the schematic illustration of FIG. 3a as arrows. A support moment $M_b$-$M_{counter}$ resulting when bending the detector 32 by means of the bending moment $M_b$ is absorbed by the two linear guides $36a$ and $36i$.

An effective support distance $l_{38a\_38i}$ (distance between the linear guides $36a$ and $36i$) also varies by the bending, which is compensated by the linear guides $36a$ and $36i$. In order for the X-ray detector 32 not to shift due to the bending moment $M_b$ or to remain centered, the X-ray detector 32 in accordance with further embodiments may include a further linear guide $36e$ which guides the center detector module $32e$ to be parallel to its normal to surface or perpendicular to the linear guides $36a$ and $36i$. This ensures precise focusing or orienting the focus of the X-ray detector 32. It is also to be mentioned that a differing support and introduction of force would also be feasible for adjusting the normals to surface. One alternative for bending the X-ray detector 32 would be varying or shortening the distance $l_{38a\_38i}$ directly.

Figure 4A:
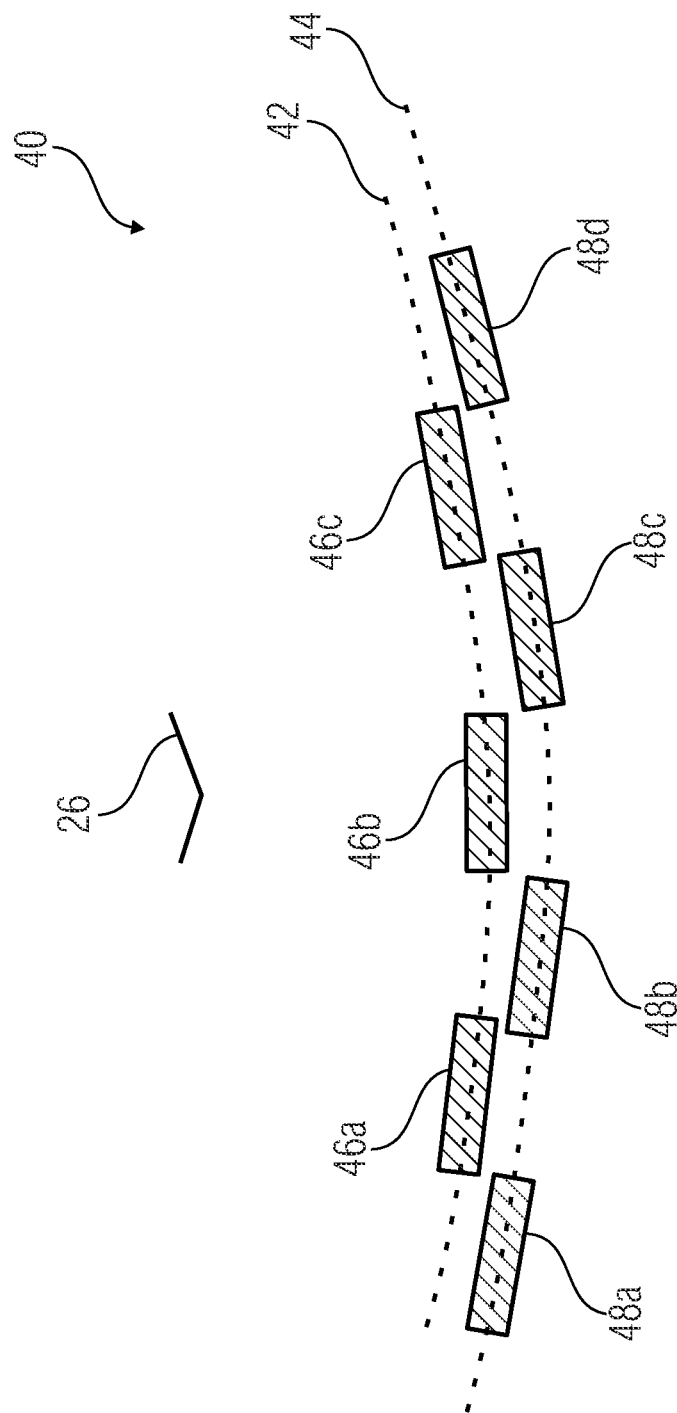
FIG. 4a shows a schematic basic illustration of an X-ray detector having two radii of curvature according to another embodiment.

FIG. 4a shows another embodiment of an X-ray detector 40 in which the individual detector modules are arranged on two different coaxial circular paths 42 and 44. Three detector modules $46a$, $46b$ and $46c$ are arranged on the circular path 42 comprising the smaller radius of the two circular paths 42 and 44. In contrast to the embodiments discussed above, the detector modules $46a$, $46b$ and $46c$ here are not neighboring or adjacent directly, but arranged spaced apart from each other with gaps therebetween. The distances or gaps exhibit approximately the width of the individual detector modules $46a$, $46b$ and $46c$ or, advantageously, a smaller width than the detector modules on the second circular path 44. Four detector modules $48a$, $48b$, $48c$ and $48d$ on the second circular path 44 are offset to the detector modules $46a$, $46b$ and $46c$, i.e. are arranged in the gaps or next to the detector modules $46a$, $46b$ and $46c$.

Due to this offset arrangement, the detection planes lying next to one another are located on two different circular paths 42 and 44 such that the entire detection region may be detected by means of the detector modules 48a, 46a, 48b, 46b, 48c, 46c and 48d. This embodiment of detector modules arranged on coaxial circular paths 42 and 44 of different radii offers the advantage that the individual detection regions of the detector modules 48a to 48d and 46a to 46c overlap, so that no "non-detection regions" or "dead regions" which are exemplarily caused by the flexible support between two neighboring detector modules result.

According to the above embodiments, due to the coaxial arrangement, the respective normals to surface of the detector modules 48a to 48d and 46a to 46c meet in the focal spot of a radiation source (not illustrated), wherein there is no uniform focus-detector distance due to the two radii of the circular paths 42 and 44. In analogy to the above embodiments, the radii of the circular paths 42 and 44 and, thus, the normals to surface relative to one another or the angle between the normals to surface are adjustable. With regard to manipulation means and support, such a detector 40 basically corresponds to the setup discussed in FIG. 3, but is of considerably higher complexity.

Figure 4B:
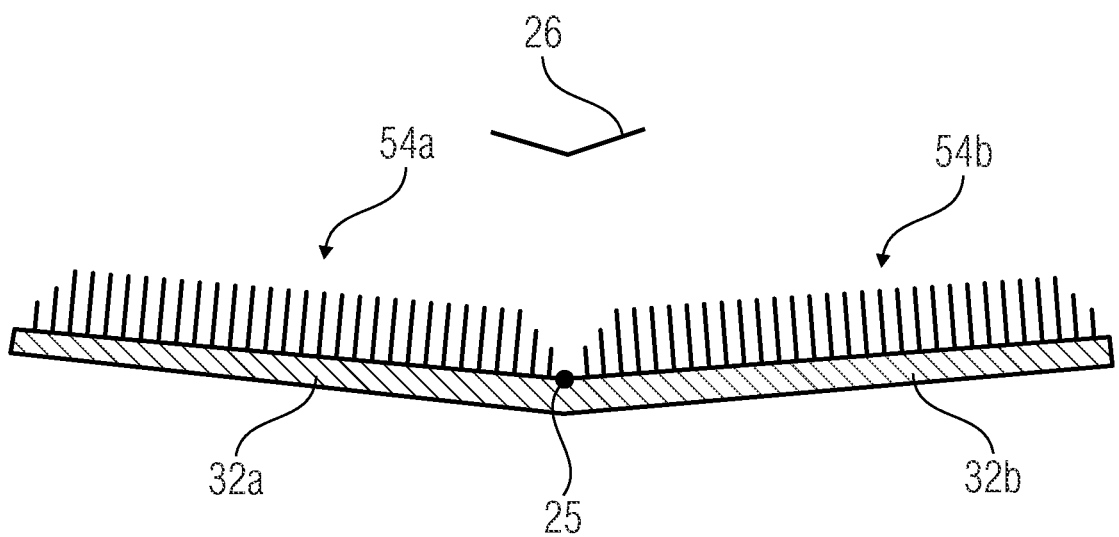
FIG. 4b shows a schematic basic illustration of an X-ray detector including applied scattered radiation grids in accordance with an embodiment.

In correspondence with the embodiment of FIG. 1, FIG. 4b shows two detector modules arranged on a circular path 32a and 32b. Also corresponding to the embodiment of FIG. 1, the two detector modules 32a and 32b are supported to be rotatable around the center of rotation 25. In contrast to the embodiment of FIG. 1, the detector modules 32a and 32b each comprise a scattered radiation grid 54a and 54b, respectively, on the side of the detection regions, i.e. on that side facing the radiation 26. The scattered radiation grids 54a and 54b include sheets arranged in parallel each extending perpendicularly from the respective detection plane, i.e. in the direction of the normals to surface. The scattered radiation grids 54a and 54b may extend either in a first and a second direction (perpendicular to the respective normals to surface and perpendicular to the first and second directions) or along the third and fourth directions (tangential to the circular path and perpendicular to the respective normal to surface). The scattered radiation grids 54a and 54b comprise sheets or lamellae made of a highly absorbing material, such as, for example, lead or tungsten, wherein a film material which is nearly transparent for X-radiation may be present in the gaps.

Due to the subdivision of the entire detector 32 in several detector modules 32a and 32b, the solid angle used per detector module 32a and 32b is small. The scattered radiation grids 54a and 54b do not limit the solid angle used further such that the radiation impinges nearly perpendicularly (even in the edge regions of the detector modules 32a and 32b) and scattered radiation may be filtered out, thereby increasing the image quality or the contrast sensitivity achievable. Due to the variable relative arrangement of the detector modules 32a and 32b, the scattered radiation grids 54a and 54b may be arranged to be perpendicular to the respective image detection planes for all detector modules 32a and 32b, which, compared to conventional scattered radiation grids which must be arranged to be orientated to the focal point of the X-radiation at an angle, means a considerable reduction in the manufacturing complexity. Consequently, scattered radiation grids 54a and 54b of this kind may also be employed when using X-ray systems industrially since they no longer restrict the detector to a certain focus-detector distance, as has been the case.

Since the influence of the vertical scattered radiation is low, advantageously the scattered radiation grid 32a and 32b is arranged only in the first or second direction, i.e. perpendicular to the circular path, in order to keep the fill factor of the pixels as large as possible or cause minimum shadowing. The cause of the larger influence of horizontal scattered radiation can be attributed to the dimensions of the detector modules 32a and 32b discussed referring to FIG. 2.

Since the center of rotation 25 of the detector modules 32a and 32b is at the front edge of the sensor modules 32a and 32b, the scattered radiation grids 54a and 54b would limit the range of motion of the detector modules 32a and 32b. In order to avoid this, according to further embodiments, the scattered radiation grids 54a and 54b are tapered towards the detector edge or rotational axis 25. It is to be mentioned that the portion of the scattered radiation detected in the edge regions may increase slightly by the tapering, however, these effects being restricted to a few pixels in the edge region and, consequently, being low.

With regard to the arrangement of the scattered radiation grids 54a and 54b in the first and second or third and fourth directions, it would alternatively be possible for the scattered radiation grids 54a and 54b to be arranged both in the first and third directions or both in the second and fourth directions, thus forming a two-dimensional square grid.

A setup example of an X-ray detector 32 is described referring to FIGS. 5a to 5e, wherein this X-ray detector 32 basically corresponds to the X-ray detector 32 shown in FIG. 3.

The X-ray detector 32 illustrated in FIG. 5 comprises a plurality of detector modules 32a to 32i connected to one another flexibly, advantageously in an odd number. The plurality of detector modules 32a to 32i is arranged on a base plate 58 which is exemplarily produced by means of aluminum pressure casting. Each of these detector modules 32a to 32i comprises different elements, such as, for example, a sensor board, a collimator and/or a connective spring, as will be discussed in greater detail referring to FIG. 5b. The plurality of detector modules 32a to 32i supported relative to one another which are supported by three linear supports 36a, 36i and 36e relative to the base plate are arranged along a circular arc, wherein the radius may be varied by electrical manipulation means which may exemplarily comprise two electric motors. The manipulation means will be discussed in greater detail referring to FIG. 5d, wherein the support 36a or 36i will be discussed in greater detail referring to FIG. 5c.

In accordance with the above embodiment of FIG. 3, the torque $M_b$ is introduced by means of the manipulation unit at the outer ends, i.e. at the detector modules 32a and 32i which are guided by means of the linear supports 36a and 36i. The linear supports 36a and 36i are arranged such that the detector modules 32a and 32i are movable alongside the base plate, wherein the linear support 36e is arranged such that the center detector module 32e is movable in a transverse direction, i.e. along its normal to surface. In analogy to the embodiment of FIG. 3, the linear supports 36a and 36i serve for supporting a torque $M_b/2$ introduced exemplarily at the point of the linear support(s) 36a and/or 36i, whereas the linear support 36e serves the purpose of the focus of the X-ray detector 32 not to shift laterally (exemplarily as a result of a torque $M_b$ introduced) relative to the X-ray source (not illustrated). In other words, this means that the linear support 36e supports the detector module 32e (and thus the entire X-ray detector 32) such that it may not be shifted in a longitudinal direction, but only in a transverse direction along its normal to surface. Consequently, it is of advantage for the X-ray detector 32 to comprise an odd number of detector modules in order for same to be guided in the center or centrally by means of the central detector module 32e thereof.

Figure 5A:
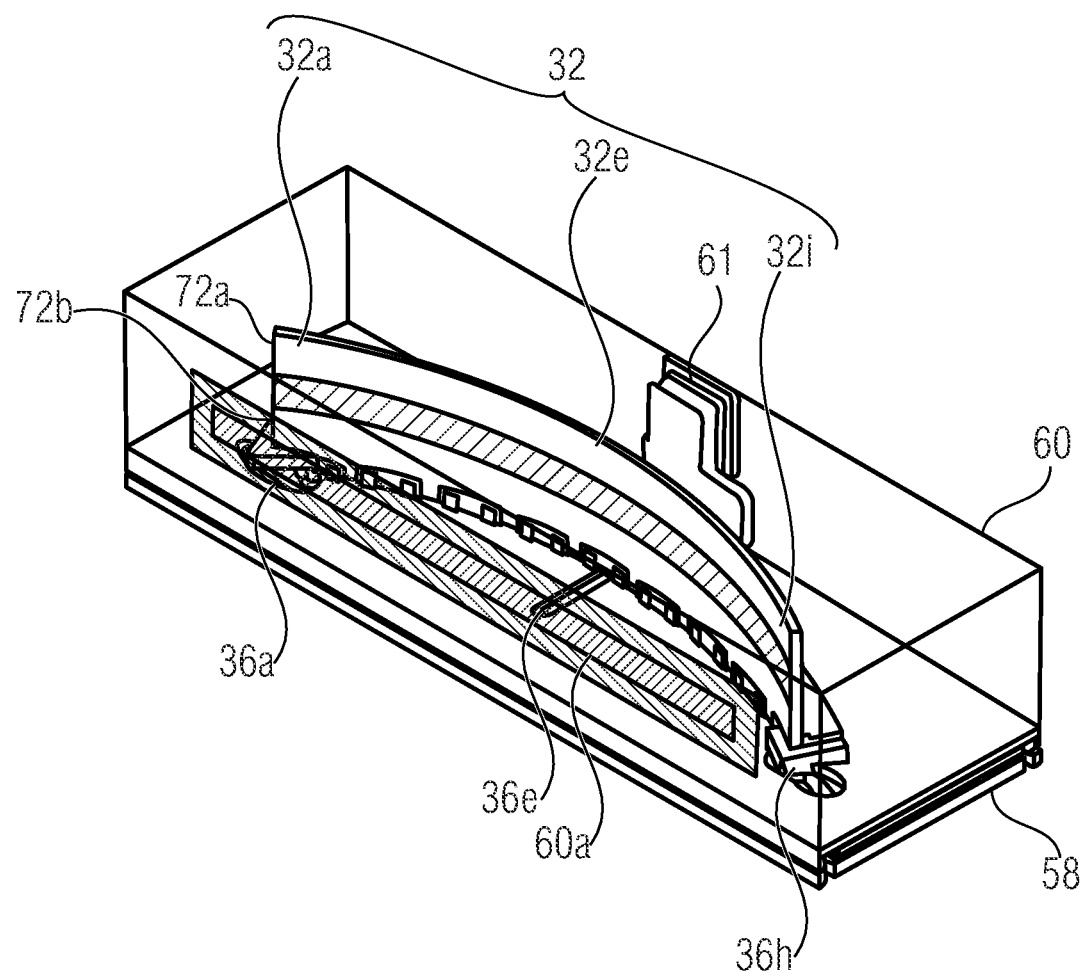
FIGS. 5a-5e show a setup example of an X-ray detector in accordance with an embodiment, with detail views and a flowchart for illustrating the process of adjusting the detector modules.

In accordance with further embodiments, the X-ray detector 32 illustrated in FIG. 5a which is mounted on the base plate 58 may also comprise a casing 60 which is mounted on the base plate 58 as a lid. The casing 60 serves for protecting the sensor boards and sliding surfaces from dust and dirt. In order to nevertheless allow unlimited detection of X-radiation, the casing 60 comprises a radiation-transmissive region or viewing window 60a which extends along the entire detection region of the X-ray detector 32 (on the side facing the X-ray source) and may exemplarily comprise a Kapton film, carbon fiber plastic (CFP) or a thin metal sheet. In correspondence with further embodiments, a cooling system 61 may be provided at the casing 60 for (air) conditioning the X-ray module.

Figure 5B:
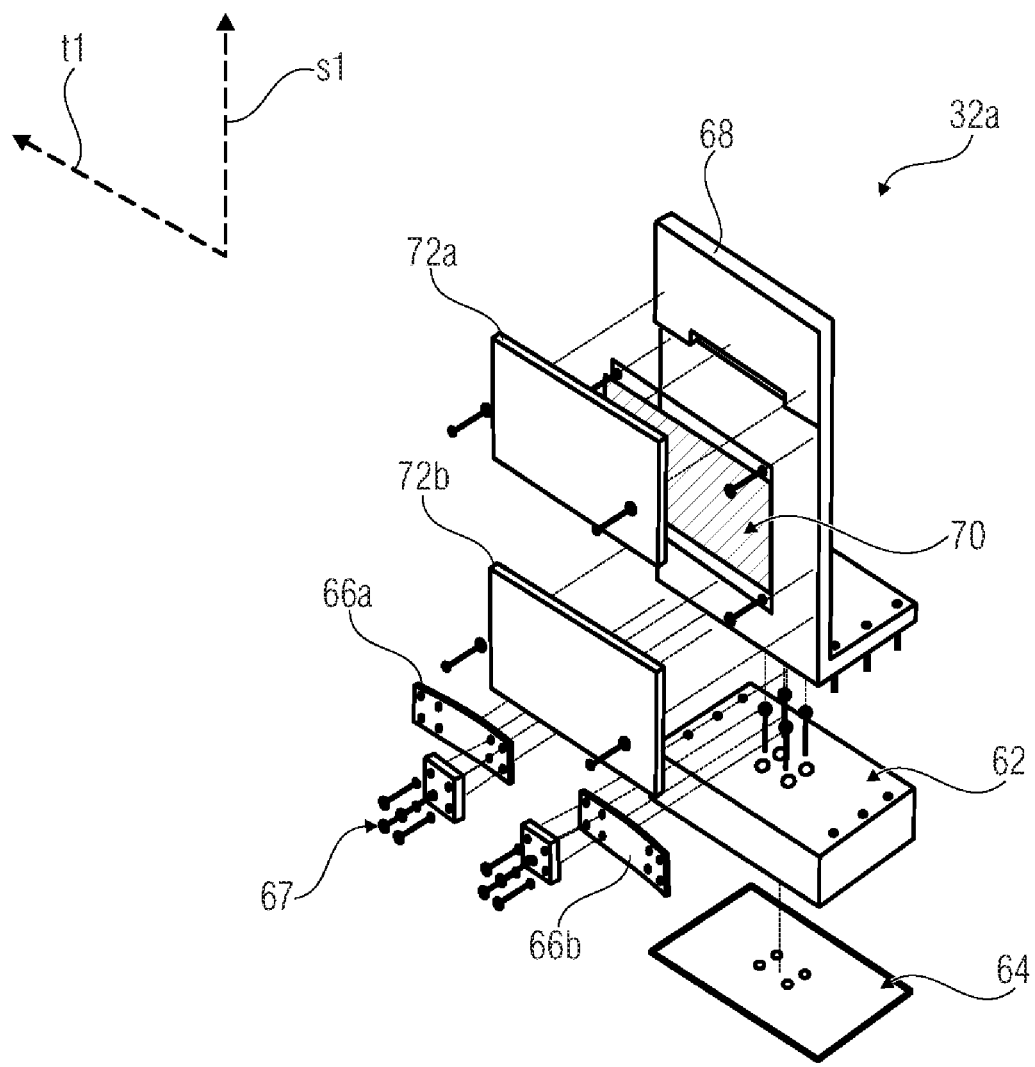

FIG. 5b shows one of the detector modules 32a to 32i in an exploded view. The detector module 32a illustrated comprises a module carrier 62 which is supported to be shiftable on the base plate (not illustrated) by means of a plate 64 (for example a Permaglide™ plate or Glycodur™ plate) which exemplarily includes polytetrafluoroethylene (Teflon™) so as to minimize friction. Additionally, two springs 66a and 66b are mounted to the module carrier 62. The two springs 66a and 66b are mounted at two opposite sides of the module carrier 62 so as to produce a flexible connection to the neighboring detector module both on the one and the other side. These springs 66a and 66b take the function of a hinge and serve for transmitting the torque. It is to be mentioned in addition that the springs or connective springs 66a and 66b in this embodiment are arranged on the inner side of the X-ray detector 32 which may be bent along an arc, which allows minimizing the so-called "dead region". Optionally, it would also be feasible for further springs, such as, for example, coil springs, to be used for additionally stabilization.

A sensor board carrier 68 on which a sensor board 70 is mounted is mounted on the module carrier 62. Optionally, two collimators 72a and 72b are provided at the sensor carrier 68 in front of the detection region of the sensor board 70, the collimators serving for generating a parallel path of the X-radiation incident on the sensor board 70. As is illustrated in FIG. 5a, the collimator 72a or the collimator 72b may be arranged in the edge regions of the sensor board 70 such that only the sensor area is irradiated. All the detector electronics are arranged behind the collimators, for protection from X-radiation.

Figure 5C:
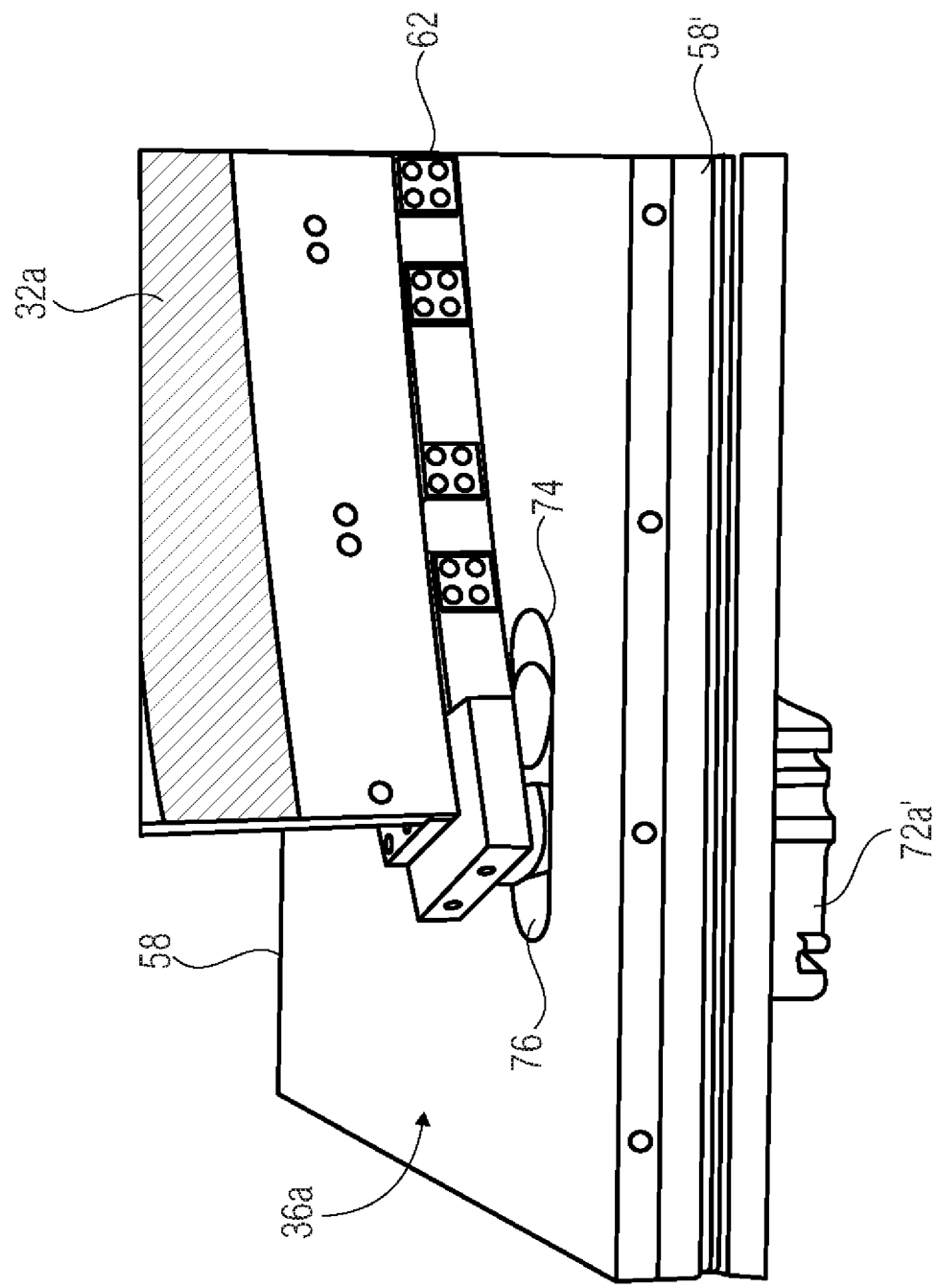

FIG. 5c shows a detailed view of manipulation means 72a' in connection with the linear guide 36a provided at the first detector module 32a. The manipulation means 72a' is arranged below the base plate 58 and transmits the torque to the module carrier 62 of the detector module 32a by means of a shaft 76. Since the radius of curvature and thus the longitudinal position of the detector module 32a change when introducing a torque by means of the manipulation means 72a', the shaft 76 is guided through the base plate 58 by means of a longitudinal hole 74. Longitudinal motion and thus the smallest possible radius of curvature are limited by the length of the longitudinal hole 74. This linear guide 36a is illustrated in greater detail in FIG. 5d.

Figure 5D:
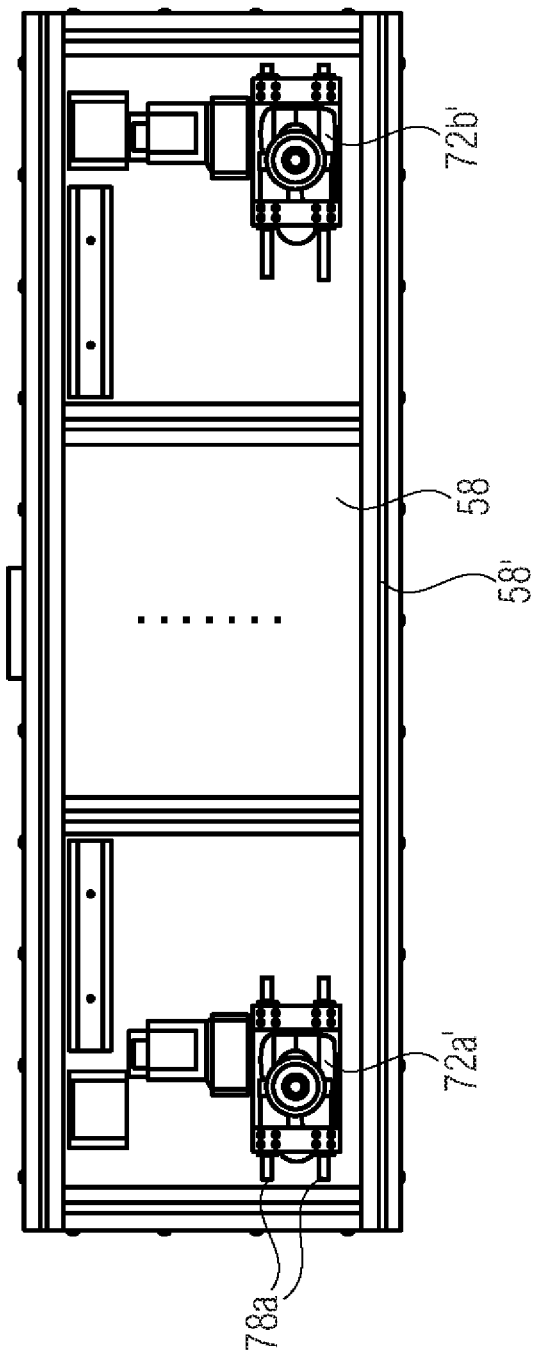

FIG. 5d shows the base plate 58 from below, wherein the electric motors of the manipulation means 72a' and manipulation means 72b' (at the position of the linear guide 36i) are illustrated here. Subsequently, the manipulation means 72a' will be discussed, also representing the manipulation means 72b'. The manipulation means 72a' is mounted on the lower side of the base plate 58 by means of two parallel rails 78a arranged alongside the base plate 58. On the one hand, the manipulation means 72a' and, thus, the X-ray module 32a may be shifted longitudinally or guided longitudinally by the longitudinal orientation of the rails 78a and, on the other hand, the torque of the manipulation means 72a' may be supported by the rails 78a. The rails 78a may exemplarily be implemented as swallow-tail rails. Additionally, it is to be mentioned that the base plate 58 may be reinforced by a frame 58' in order to avoid bending thereof.

Figure 5E:
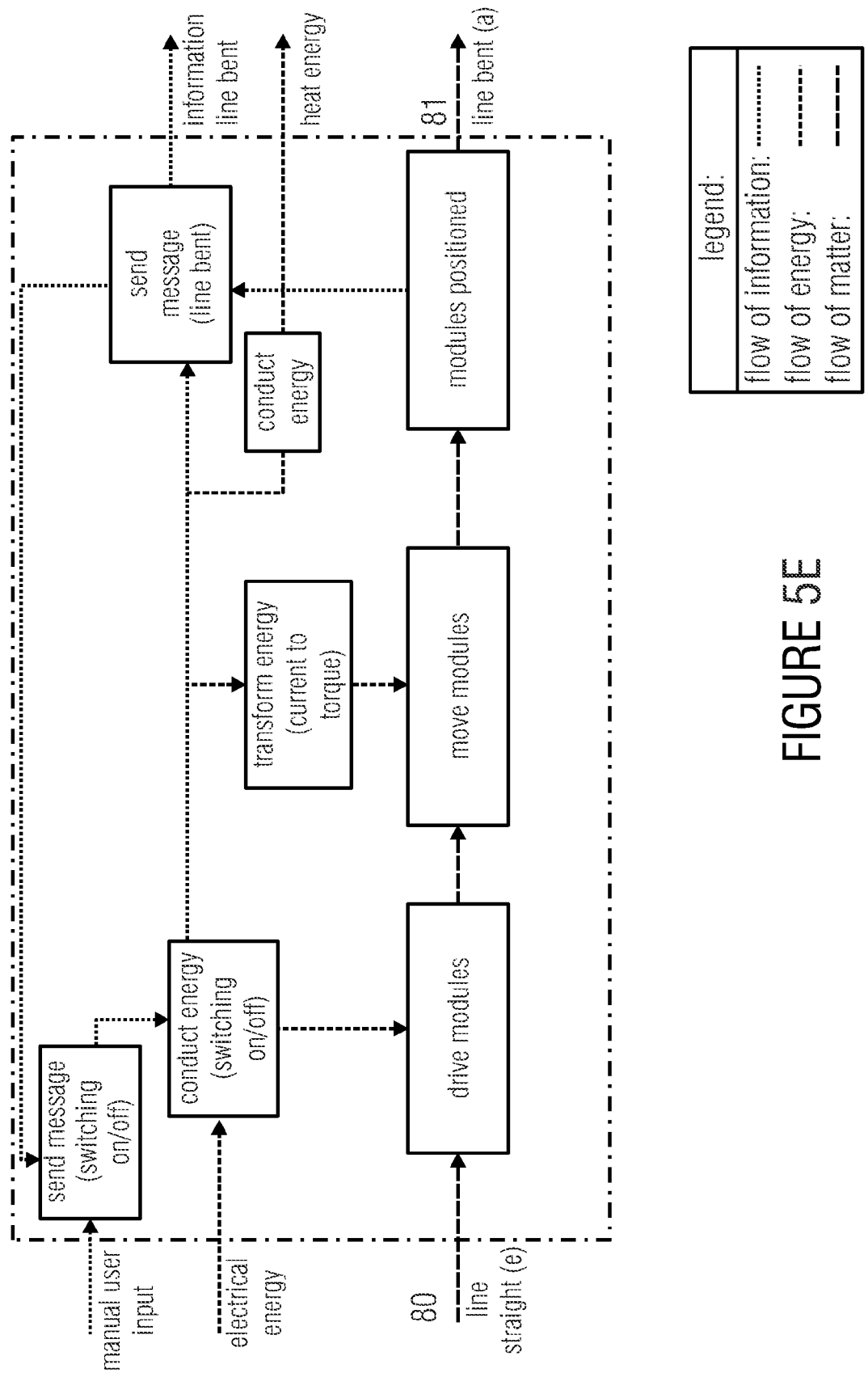

FIG. 5e shows a flow chart for illustrating adjusting the radius of curvature of the flexible X-ray module 32. A "non-bent (i.e. straight) X-ray module" is assumed to be the starting state 80. In order to put this state to the desired final state "X-ray module bent" 81, the modules are driven and moved until positioned correspondingly. The user performs a manual input which determines the predetermined final position or final state 81. The electric motors are driven or supplied with electrical energy by the input until the final position 81 is reached. In accordance with further embodiments, the X-ray detector here may comprise a positional sensor which transfers to the controller information indicating that the lines are bent or the final position has been reached. Then, the electrical energy and, thus, the torque $M_b$ for electric motors are no longer increased such that the final position 81 reached is maintained, wherein the final position 81 is principally defined by a torque equilibrium ($M_b - M_{counter} = 0$), wherein the torque $M_b$ introduced by means of the electric motors corresponds to the torque $M_{torque}$ generated in particular by the springs. The information of the final position having been reached is also output to the user. In accordance with further embodiments, the manipulation means may also include stepper motors which are switched off and fixed when the final position has been reached.

Different alternative manipulation means will be discussed below referring to FIG. 6.

Figure 6A:
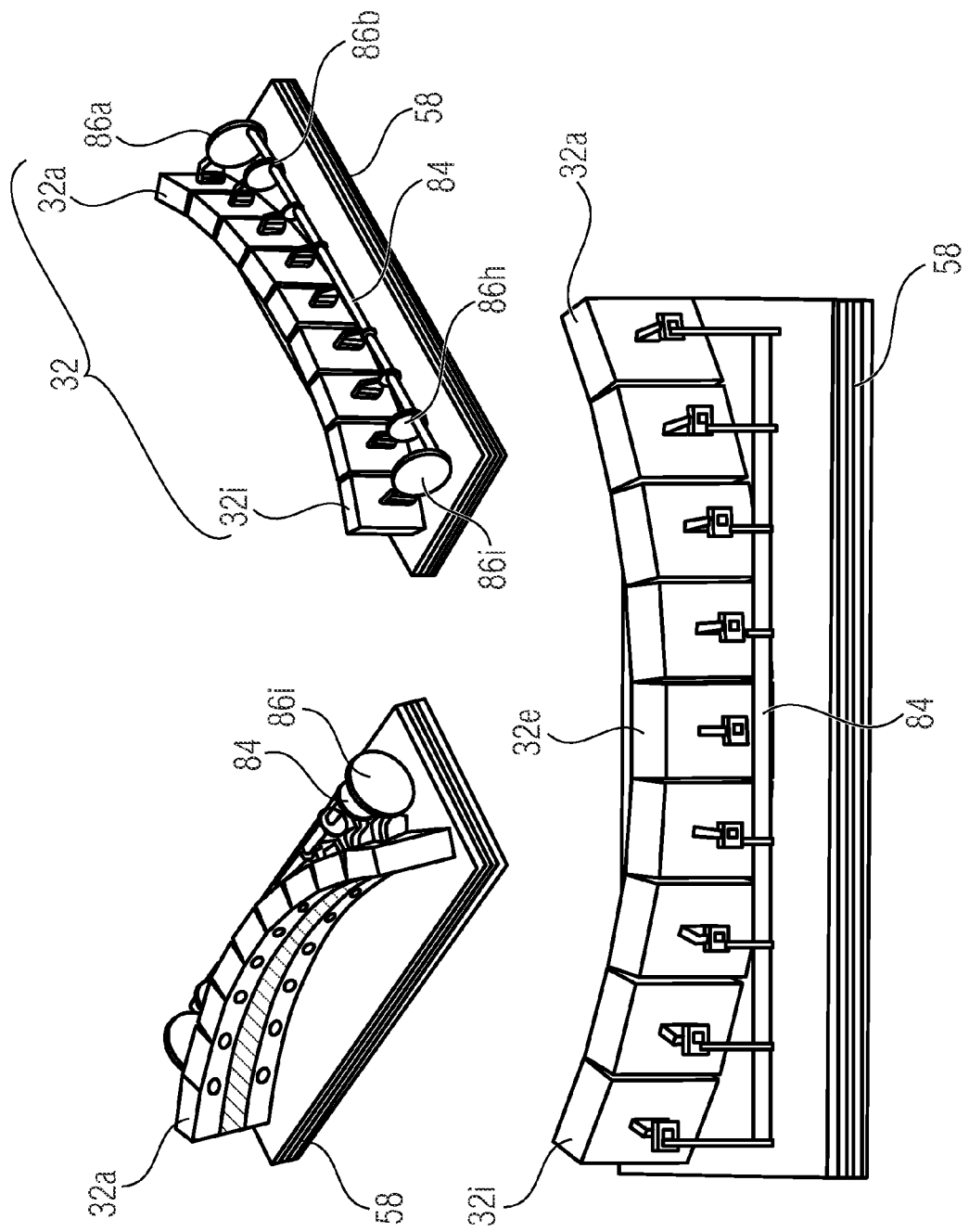
FIGS. 6a-6d show different setup examples of manipulation means in accordance with embodiments.

FIG. 6a shows three views of the X-ray detector 32 arranged on the base plate 58. The radius of curvature of the X-ray detector 32 here is realized by manipulation means 84 which is implemented as an eccentric shaft 84. The eccentric shaft 84 is arranged along the X-ray detector 32 on the back side thereof and comprises for each detector module 32a to 32i eccentric discs 86a to 86i of different sizes which are implemented either to be eccentric (i.e. oval) discs or circular discs which, however, are suspended eccentrically (in the edge region). The most distant eccentric discs, i.e. 86a and 86i for the detector modules 32a and 32i, are the largest, i.e. larger than the more central eccentric discs 86b and 86h for the detector modules 32h and 32b, wherein the central detector module 32e has no eccentric discs. In other words, with regard to their position and relative size, the eccentric discs 86a and 86i are dimensioned relative to each other.

Since the eccentric discs 86a to 86i are engaged with the detector modules 32a to 32i, the detector modules 32a to 32i are shifted (transverse to the base plate 58) when turning the eccentric shaft 84. The shift is different for each detector module 32a to 32i, since the eccentric discs 86a to 86i comprise different diameters. Here, all the detector modules 32a to 32i, except for the central detector module 32e, are shifted, since the normal to surface thereof will be directed to the focal spot of the radiation source (as long as the X-ray detector 32 is positioned correctly relative to the radiation source). The detector modules 32a to 32i are arranged along a circular path due to the diameters of the eccentric discs 86a to 86i becoming smaller towards the center, wherein they are twisted as a result of the elastic connection of the detector modules 32a to 32i. Shifting and, thus, twisting here are dependent on the angular position of the eccentric shaft 84. In correspondence with further embodiments, the detector modules 32a to 32i may also comprise an engagement portion on the back side which may be implemented using a joint.

Figure 6B:
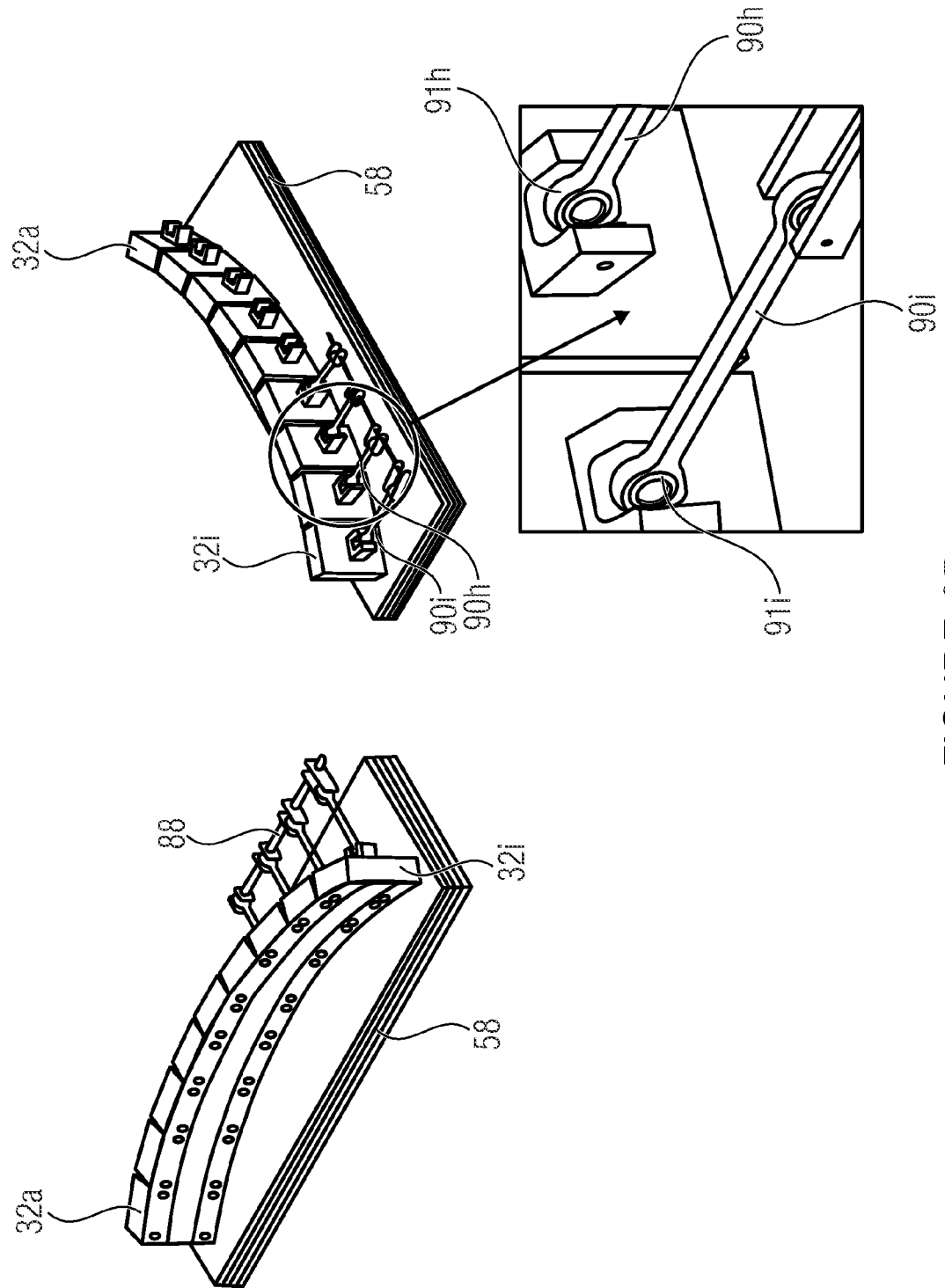

FIG. 6b shows three views of the X-ray detector 32 arranged on the base plate 58 which in this embodiment is adjusted by manipulation means 88. The manipulation means 88 comprises a crank shaft 88 having pushers (connecting rods) 90a to 90i of different lengths. In correspondence with the embodiment of FIG. 6a, the outer pushers are longer relative to the more central pushers. This means that pusher 90i connected to the detector module 32i is longer than pusher 90h connected to the detector module 32h which, with a variation of the angular position of the crank shaft 88, results in a more extensive shift on the base plate 58 or a larger twisting of the detector module 32i (cf. FIG. 6a). As shown in the enlarged illustration of pushers 90i and 90h, the pushers are hinged to the detector modules by means of ball ends 91i and 91h, respectively. Additionally, it is to be mentioned that the crank shaft 88 may be cranked using different dimensions.

It is mentioned with regard to FIGS. 6a and 6b that both a rotary motion of the detector modules 32a to 32i and a translatory motion of the detector modules 32a and 32i takes place because the detector modules 32a to 32i are oriented along a circular arc. The translatory motion is caused directly by the manipulation means 84 and 88, whereas the rotary motion, i.e. introducing the bending moment, takes place because the individual detector modules 32a to 32i are supported relative to one another.

Figure 6C:
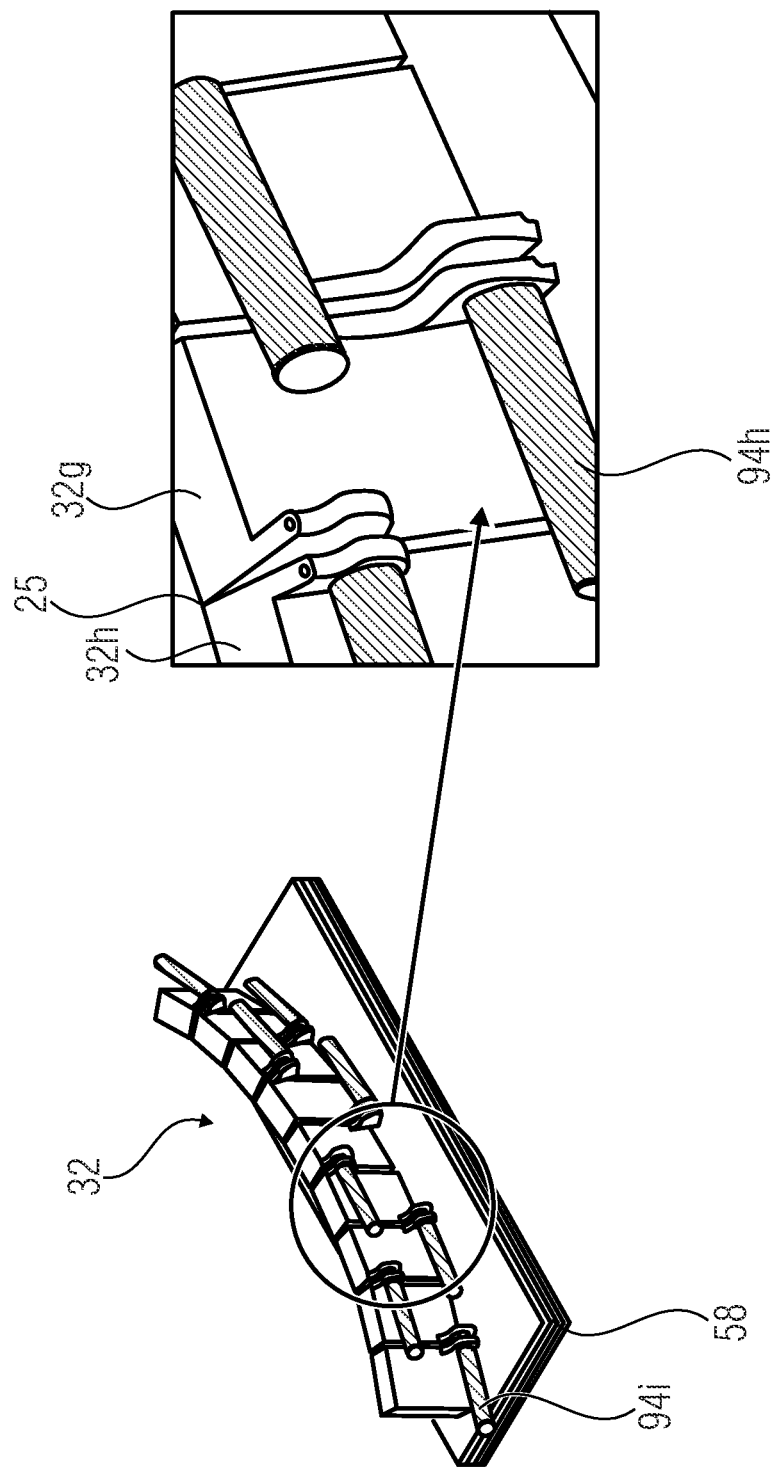

FIG. 6c shows two views of another embodiment of manipulation means, wherein linearly variable elements 94a to 94i are provided between the individual detector modules 32a to 32i of the X-ray detector 32. These elements 94a to 94i are variable in their lengths, which are also referred to as linear actuators, are arranged on the back side, i.e. using a lever arm relative to the rotational axis 25 (abutting edge of the two detector modules 32a and 32g).

The mode of functioning of the linearly variable elements 94a to 94i will be discussed below using the linearly variable element 94h arranged between the detector modules 32g and 32h. With a variation in length or a force introduced in the linearly variable element 94, a torque is introduced into the two linear modules 32h and 32g, the result being tilting or twisting of the two detector modules 32g and 32h. Since the linear actuators are provided each between two detector modules, all the detector modules 32a and 32g may be arranged along the circular path.

Figure 6D:
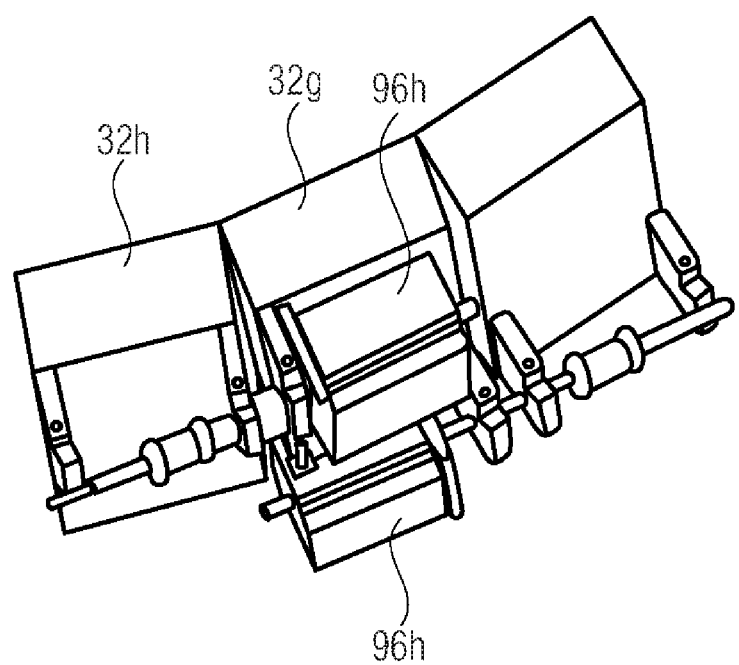
Figure 7:
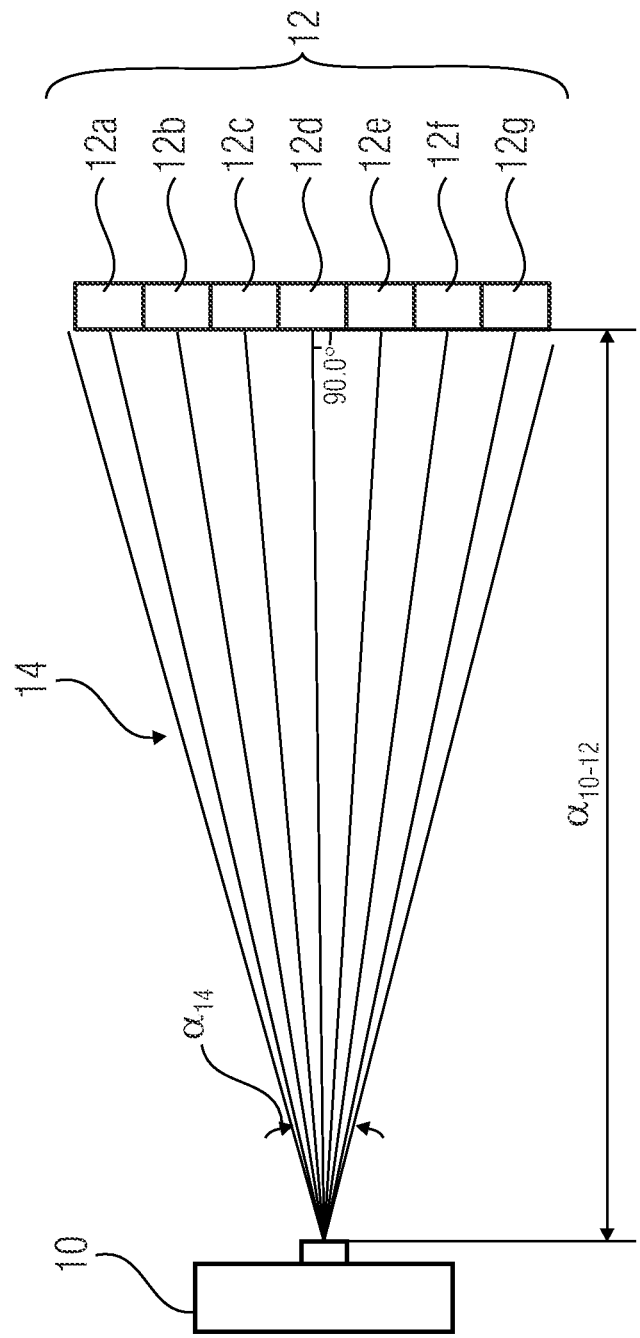
FIG. 7 shows a schematic basic illustration of a known X-ray detector.

FIG. 6d shows another potential embodiment of the manipulation means described in FIG. 6c. A linearly variable element 96h which comprises a stepper motor and a spindle having bellows coupling is arranged between two detector modules 32g and 32h. The stepper motor arranged at the one detector module 32g varies the distance and, thus, tilting of the two detector modules 32g and 32h when rotating via the spindle which is engaged with the further detector module 32h via a thread. The bellows coupling provided optionally here prevents tension in the thread which may result from tilting of the two detector modules 32g and 32h.

It is to be mentioned with regard to FIGS. 6a to 6d that the eccentric shaft 84, the crank shaft 88 and the linearly variable elements 94a to 94i and the linearly variable elements 96a to 96i may be driven both electrically, for example by means of an electric or stepper motor, and mechanically, for example by means of a manual crank. It would also be feasible for the angle variation or variation in the radius or curvature to be realized by means of a pneumatic or hydraulic system (for example, pneumatically driven linear actuators). It is also to be mentioned that other kinds of introducing torque may exemplarily be implemented by means of a plug system (which includes distance or angular elements of a modular setup).

It is also to be mentioned referring to FIG. 5b that the springs 66a and 66b may also be realized by simple hinges or by other bendable elements, wherein the connection between two neighboring detector modules is advantageously free of backlash. Alternatively, it would also be conceivable to use rollers or other friction-minimized supports, instead of the Permaglide pad 64.

It is also be to be mentioned that the aspects having been discussed referring to FIGS. 4b, 5a to 5e and 6a to 6d may also be applied to the embodiment of FIG. 4a, wherein the detector modules are arranged on different coaxial circular paths, i.e. offset to one another.

The invention will be summarized below in other words: A method for being able to make use of the advantages of a curved detector in a flexible industrial X-ray system has been developed, which allows the radius of curvature to be adjusted flexibly. The fact that the radius of curvature may be adjusted flexibly is the main innovation of this invention report. Furthermore, the setup allows simply using a scattered radiation grid. Thus, the concept is also suitable for a large number of modules. This is to be discussed using an exemplary system. The arrangement is, as shown in FIG. 2, similar to that in conventional systems, however, the individual detector modules are supported to be movable and connected to one another via a flexible mechanic connection. With this concept, the radius may exemplarily be adjusted via two motors and three linear guides, as is shown in FIGS. 3a to 3c.

The modular setup of the detector modules is realized by means of so-called modular units. These are arranged on the base plate in an odd number (cf. FIG. 5a). In order for only very small gaps (and thus no dead regions, if possible) to exist in the detector, it is of advantage for the modules to be placed next to one another as closely as possible (cf. FIG. 1). The sensors of the detector modules adjacent to each other are placed such that they nearly contact each other at the corner on the side facing radiation. This point of contact at the same time is the center of rotation around which the modules move when adjusting the radius of curvature of the detector. From a mechanical point of view, the center of rotation is placed exactly at that location by the spring having its bending point there and being placed correctly by means of spacers.

The modular units are located on a base plate made of aluminum cast. In order to minimize friction, a plate made of Permaglide (polytetrafluoroethylene (PTFE)) is mounted below the modular carrier. The module carriers are connected to one another using connective springs. Apart from the setup shown in the explosive view, another spring may also be used above the sensor surface, for additional stabilization. The springs take the function of a hinge and serve for transmitting torque. The torque is introduced at the outer ends via two drives. The drives are guided via linear guides. The modular unit in the center is also guided by a linear guide. Bending the connective spring at an even bending moment allows adjusting a circular arc using only two motors.

The drives are located below the base plate and are also guided by linear guides. In order to prevent the base plate from bending, the base plate is reinforced using a frame. In order to protect the sensor board and the gliding surfaces from dust and dirt, the setup is covered by a casing which comprises a radiation-transmissive window, such as, for example, Kapton film, CFP or a thin metal sheet, and comprises a cooling system.

A detector set up without any gaps at all could also be realized. A modular arrangement in two rows would, for example, be of advantage here, as is shown in FIG. 4a. Such a detector, however, would entail a mechanically more complex setup. In addition, due to the two "layers", it no longer comprises a uniform radius or focus-detector distance.

The concept developed here wherein each detector module is oriented perpendicular to the location of the X-ray source, also allows an easily realizable scattered radiation grid which at the same time may be used flexibly. FIG. 4b shows the setup of a scattered radiation grid in top view. The scattered radiation grid includes sheets arranged in parallel. A filling material which is nearly transparent for X-radiation may be present between these sheets. The sheets should be made of a highly absorbing material, such as, for example, lead or tungsten. This simple parallel arrangement is possible since the solid angle used per detector module is very small and, thus, the radiation impinges almost perpendicularly, even at the edge regions of the module. Due to the curved setup, this situation is the same for each detector module, irrespective of its position.

The scattered radiation grid, however, does not only absorb scattered radiation, but also part of the primary intensity. Since the scattered radiation grid hides part of the active pixel area or scintillator, the filling factor thereof decreases. The proportion of covered pixel area is dependent on the thickness of the absorbing sheets. This thickness in turn depends on the energy of the X-radiation.

The concept developed here is primarily aimed at one-line or multi-line detectors but not area detectors. Since the solid angle used in these detectors is very broad, but its height is very flat, the proportion of the scattered radiation impinging on the detector from a horizontal direction is considerably larger than from the vertical direction. The proportion of the horizontally directed scattered radiation may be caught by a vertical grid. Another horizontal grid would be necessitated for intercepting the vertical scattered radiation, the result here would be a square grid. Since the influence of the vertical scattered radiation, however, is low and in order to keep the filling factor of the pixel as large as possible, a horizontal grid may be omitted.

Since the center of rotation of two detector modules is the front corner point of the sensors, the scattered radiation grids would contact each other at the detector module edges. In order to prevent this, they are tapered towards the detector edge. However, the proportion of scattered radiation detected in this region increases slightly. This effect increases towards the detector module edge. Thus, the contrast sensitivity achievable is reduced slightly towards the module edges. In conventional detector setups, the effect should be limited to a few pixels. Compared to a detector with no scattered radiation grid, this setup offers great advantages for the contrast sensitivity achievable.

The setup described allows adjusting the radius of curvature of the detector. This allows using a focused detector with flexible requirements. The oblique transmission may be minimized by the radial arrangement and a uniform focus-detector distance can be achieved for all detector modules. The disadvantages described at the beginning are eliminated by this and the image quality, in particular in the edge regions, may be improved considerably compared to a straight line or area detector. Furthermore, the setup described allows practical usage of a scattered radiation grid, which may further increase image quality.

The largest flexibility possible is achieved when using the modular units. Due to the usage of connective springs, a freely adjustable, straight and radial arrangement is made possible using two drives only.

The invention is typically applied in X-ray detectors which are used in industrial X-ray examination systems which are provided for examining different objects. Thus, the invention may be applied both in X-ray detectors having only a single line, so-called line detectors, and detectors having many lines, so-called multi-line detectors. Due to the modularity, the detector here may be length-adjusted to the requirements. The invention may thus be used for both X-ray detectors of low X-ray energy and X-ray detectors of high X-ray energy.

While this invention has been described in terms of several embodiments, there are alterations, permutations, and equivalents which will be apparent to others skilled in the art and which fall within the scope of this invention. It should also be noted that there are many alternative ways of implementing the methods and compositions of the present invention. It is therefore intended that the following appended claims be interpreted as including all such alterations, permutations, and equivalents as fall within the true spirit and scope of the present invention.

The invention claimed is:

1. An X-ray detector comprising:
   a first detector module including a first detection region arranged in a first detection plane;
   a second detector module including a second detection region arranged in a second detection plane, which is movably attached to the first detector module; and
   a manipulator that orients the first detection plane of the first detector module and the second detection plane of the second detector module to each other such that a first normal to a surface of the first detection plane and a second normal to a surface of the second detection plane intersect within a reference region; wherein
   the X-ray detector includes at least a further detector module including a further detection region arranged in a further detection plane, which is arranged relative to the first detector module and the second detector module such that the first detection plane, the second detection plane, and the further detection plane are distributed with their respective centroids tangentially on a circular path at an adjustable radius;
   the manipulator orients the further detection plane of the further detector module relative to the first detection plane and the second detection plane such that the first normal and the second normal to the surfaces of the first detection plane and the second detection plane, together with a further normal to a surface of the further detection plane, intersect within the reference region;
   the manipulator provides the first detector module and/or the further detector module with a torque; and
   the first detector module, the second detector module, and the further detector module are supported relative to one another by springs that distribute the torque evenly among all the first detector module, the second detector module, and the further detector module in order to orient the first detector module, the second detector module, and the further detector module along the circular path.

2. The X-ray detector in accordance with claim 1, wherein the first detector module, the second detector module, and the further detector module are coupled to one another such that, when adjusting the radius, an adjustable angle between the first normal and the second normal to the surfaces of the first detection plane and the second detection plane corresponds to an adjustable angle between the second normal and the further normal to the surfaces of the second detector plane and the further detection plane.

3. The X-ray detector in accordance with claim 1, wherein the first detector module includes a plurality of sensor elements arranged along a first direction and grouped to form a first detector line and the second detector module includes a plurality of sensor elements arranged along a second direction and grouped to form a second detector line,
wherein the first direction and the second direction are parallel to each other.

4. The X-ray detector in accordance with claim 3, wherein a plurality of line-shaped detector modules are arranged such that the X-ray detector forms a cylindrical surface section with an adjustable radius.

5. The X-ray detector in accordance with claim 1, wherein the first detector module includes a plurality of sensor modules arranged in a first and a third direction and the second detector module includes a plurality of sensor modules arranged in a second and a fourth direction,
wherein the first direction and the second direction are parallel to each other and the third direction and the fourth directions extend along the circular path as tangents.

6. The X-ray detector in accordance with claim 1, wherein the first detector module is supported relative to the second detector module such that the first detector module and the second detector module; are rotatable relative to each other around a rotational axis for adjusting an orientation of the first normal and the second normal to the surfaces of the first detection plane and the second detection plane.

7. The X-ray detector in accordance with claim 6, wherein
the rotational axis is formed on a common edge of the first detector module and the second detector module on a side of the first detection region and the second detection region; or
the rotational axis is formed between and/or parallel to an edge of the first detector module on the side of the first detection region and an edge of the second detector module on the side of the second detection region.

8. The X-ray detector in accordance with claim 1, wherein the first detector module and the second detector module are supported relative to each other by a movable connective element.

9. The X-ray detector in accordance with claim 8, wherein the movable connective element is a spring, a hinge, or joint.

10. The X-ray detector in accordance with claim 8, wherein the movable connective element is a spring with a defined bending point that defines a rotational axis around which the first detector module and the second detector module are supported relative to each other to be rotatable.

11. The X-ray detector in accordance with claim 1, wherein the first detector module and the second detector module are connected relative to each other by a first spring and the second detector module and the further detector module are connected relative to one another by a second spring, the first spring and the second springs having equal spring stiffness.

12. The X-ray detector in accordance with claim 1, wherein
the first detector module includes a scattered radiation grid along a first direction which extends perpendicularly from the first detection plane along the first normal to the surface of the first detection plane as a plate element and the second detector module includes a scattered radiation grid along a second direction which extends perpendicularly from the second detection plane along the second normal to the surface of the second detection plane as a plate element, and
the first direction and the second direction are parallel to each other.

13. The X-ray detector in accordance with claim 1, wherein the manipulator varies an angle between the first detector module and the second detector module.

14. The X-ray detector in accordance with claim 1, wherein
the manipulator varies a distance between the first detector module and the further detector module, and
the first detector module, the second detector module, and the further detector module are connected relative to one another by springs that orient the X-ray detector along the circular path when varying the distance.

15. The X-ray detector in accordance with claim 1, wherein the manipulator includes an element of variable length between the first detector module and the second detector module that varies an angle between the first detector module and the second detector module.

16. The X-ray detector in accordance with claim 1, wherein the manipulator includes a crankshaft or eccentric shaft that varies an angle between the first detector module and the second detector module.

17. The X-ray detector in accordance with claim 1, wherein the first normal to the surface of the first detection plane is located in a centroid of the first detection region and the second normal to the surface of the second detection plane is located in a centroid of the second detection region.

18. The X-ray detector in accordance with claim 1, wherein all the detector modules are coupled to one another such that all normals to the surfaces of the respective detection planes are in a normal plane.

19. An X-ray detector comprising:
a first detector module including a first detection region arranged in a first detection plane;
a second detector module including a second detection region arranged in a second detection plane;
a further detector module including a further detection region arranged in a further detection plane; and
a manipulator that orients the first detection plane of the first detector module, the second detection plane of the second detector module, and the further detection plane of the further detector module to one another such that a first normal to a surface of the first detection plane, a second normal to a surface of the second detection plane, and a further normal to a surface of the further detection region intersect within a reference region,
wherein the first detection plane and/or the second detection plane is/are offset relative to the further detection plane and the first detection region and/or the second detection region is/are overlapped by the further detection region.

20. The X-ray detector in accordance with claim 19, wherein the first detection plane and/or the second detection plane is/are located tangentially on a first circular path and the further detection plane is located tangentially on a further circular path which is offset relative to the first circular path.

21. The X-ray detector in accordance with claim 19, wherein an orientation of the first detector module and the second detector module to each other may be adjusted by the manipulator such that the first detection plane and the second detection plane are arranged with their respective centroids tangentially on a first circular path and an orientation of the further detector module may be adjusted such that the further detection plane is arranged with a centroid tangentially on a further circular path which is arranged in a common normal plane with the first circular path.

22. The X-ray detector in accordance with claim 19, wherein the first circular path and the further circular path are arranged coaxially.

23. The X-ray detector in accordance with claim 19, wherein centers of the first circular path and the further circular path that include different adjustable radii are located in the reference region.

24. An X-ray system comprising:
an X-ray detector in accordance with claim 1; and
a radiation source,
wherein the reference region may be positioned by the manipulator in dependence on a focus-detector distance.

25. An X-ray system comprising:
an X-ray detector in accordance with claim 19; and
a radiation source,
wherein the reference region may be positioned by the manipulator in dependence on a focus-detector distance.

26. The X-ray system in accordance with claim 24, wherein a focal spot of the radiation source is within the reference region.

27. An X-ray system comprising:
an X-ray detector in accordance with claim 3; and
a radiation source,
wherein the radius of the circular path may be adjusted by the manipulator such that a focal spot of the radiation source corresponds to the center of the adjustable radius.

28. An X-ray system comprising:
an X-ray detector in accordance with claim 19; and
a radiation source,
wherein the radius of the circular path may be adjusted by the manipulator such that a focal spot of the radiation source corresponds to the center of the adjustable radius.

29. An X-ray detector comprising:
a first detector module including a first detection region arranged in a first detection plane;
a second detector module including a second detection region arranged in a second detection plane, which is movably attached to the first detector module; and
a manipulator that orients the first detection plane of the first detector module and the second detection plane of the second detector module to each other such that a first normal to a surface of the first detection plane and a second normal to a surface of the second detection plane intersect within a reference region,
wherein the X-ray detector includes at least a further detector module including a further detection region arranged in a further detection plane, which is arranged relative to the first detector module and the second detector module; such that the first detection plane, the second detection plane, and the further detection plane are distributed with their respective centroids tangentially on a circular path at an adjustable radius; wherein
the manipulator orients the further detection plane of the further detector module relative to the first detection plane and the second detection plane such that the first normal and the second normal to the surfaces of the first detection plane and the second detection plane, together with a further normal to a surface of the further detection plane, intersect within the reference region,
the manipulator provides the first detector module and/or the further detector module with a torque, and
the first detector module, the second detector module, and the further detector module are supported relative to one another by springs that distribute the torque evenly among all the detector modules in order to orient the detector modules along the circular path.

30. An X-ray detector comprising:
a first detector module including a first detection region arranged in a first detection plane;
a second detector module including a second detection region arranged in a second detection plane, which is movably attached to the first detector module; and
a manipulator that orients the first detection plane of the first detector module and the second detection plane of the second detector module to each other such that a first normal to a surface of the first detection plane and a second normal to a surface of the second detection plane intersect within a reference region,
wherein the X-ray detector includes at least a further detector module including a further detection region arranged in a further detection plane, which is arranged relative to the first detector module and the second detector module such that the first detection plane, the second detection plane, and the further detection plane are distributed with their respective centroids tangentially on a circular path at an adjustable radius; wherein
the manipulator orients the further detection plane of the further detector module relative to the first detection plane, and the second detection plane such that the first normal and the second normal to the surfaces of the first detection plane and the second detection plane, together with a further normal to a surface of the further detection plane, intersect within the reference region,
the first detector module and the second detector module are connected relative to each other by a first spring and the second detector module and the further detector module are connected relative to each other by a second spring, the first spring and the second springs having equal spring stiffness,
the manipulator varies a distance between the first detector module and the further detector module, and
the first detector module, the second detector module, and the further detector module are connected by springs that orient the X-ray detector along the circular path when varying the distance.

* * * * *